US009328378B2

(12) United States Patent
Earnshaw et al.

(10) Patent No.: US 9,328,378 B2
(45) Date of Patent: May 3, 2016

(54) METHOD OF LIBRARY PREPARATION AVOIDING THE FORMATION OF ADAPTOR DIMERS

(75) Inventors: David James Earnshaw, Walden (GB); Niall Anthony Gormley, Walden (GB); Helen Rachel Bignell, Walden (GB); Melanie Anne Smith, Walden (GB)

(73) Assignee: Illumina Cambridge Limited, Nr Saffron Walden (GB)

( * ) Notice: Subject to any disclaimer, the term of this patent is extended or adjusted under 35 U.S.C. 154(b) by 1533 days.

(21) Appl. No.: 12/309,772

(22) PCT Filed: Jul. 30, 2007

(86) PCT No.: PCT/GB2007/002865
§ 371 (c)(1),
(2), (4) Date: Nov. 16, 2009

(87) PCT Pub. No.: WO2008/015396
PCT Pub. Date: Feb. 7, 2008

(65) Prior Publication Data
US 2010/0167954 A1    Jul. 1, 2010

Related U.S. Application Data

(60) Provisional application No. 60/834,424, filed on Jul. 31, 2006.

(51) Int. Cl.
C12Q 1/68    (2006.01)
(52) U.S. Cl.
CPC ............ *C12Q 1/6855* (2013.01); *C12Q 1/6806* (2013.01); *C12Q 1/6874* (2013.01)
(58) Field of Classification Search
None
See application file for complete search history.

(56) References Cited

U.S. PATENT DOCUMENTS

| 4,719,179 | A | 1/1988 | Barany |
| 5,093,245 | A | 3/1992 | Keith et al. |
| 5,436,142 | A | 7/1995 | Wigler et al. |
| 5,508,169 | A | 4/1996 | Deugau et al. |
| 5,641,658 | A | 6/1997 | Adams et al. |
| 5,759,822 | A | 6/1998 | chenchik et al. |
| 6,045,994 | A | 4/2000 | Zabeu et al. |
| 6,060,288 | A | 5/2000 | Adams et al. |
| 6,090,592 | A | 7/2000 | Adams et al. |
| 6,107,023 | A | 8/2000 | Reyes et al. |
| 6,114,149 | A | 9/2000 | Fry et al. |
| 6,261,770 | B1 | 7/2001 | Warthoe |
| 6,287,825 | B1 | 9/2001 | Weissman et al. |
| 6,361,947 | B1 | 3/2002 | Dong et al. |
| 6,395,887 | B1 | 5/2002 | Weissman et al. |
| 7,115,400 | B1 | 10/2006 | Adessi et al. |
| 7,741,463 | B2 | 6/2010 | Gormley |
| 8,932,994 | B2 * | 1/2015 | Gormley et al. ............... 506/23 |
| 2003/0044794 | A1 * | 3/2003 | Bandaru et al. ................ 435/6 |
| 2004/0067493 | A1 | 4/2004 | Matsuzaki et al. |
| 2004/0209299 | A1 | 10/2004 | Pinter et al. |
| 2004/0259116 | A1 * | 12/2004 | Beckman et al. ............... 435/6 |
| 2005/0095645 | A1 | 5/2005 | Jones et al. |
| 2005/0100900 | A1 | 5/2005 | Kawashima et al. |
| 2006/0019274 | A1 * | 1/2006 | Goel ............................... 435/6 |
| 2006/0135458 | A1 * | 6/2006 | Vaillant et al. ................ 514/44 |
| 2006/0292597 | A1 * | 12/2006 | Shapero et al. ............... 435/6 |
| 2007/0128624 | A1 * | 6/2007 | Gormley et al. ............... 435/6 |
| 2009/0176662 | A1 | 7/2009 | Rigatti et al. |

FOREIGN PATENT DOCUMENTS

| EP | 0224126 | 6/1987 |
| EP | 1201768 A2 * | 5/2002 |
| EP | 1350853 A1 * | 10/2003 |
| GB | 2412170 | 9/2005 |
| WO | 00/23620 | 4/2000 |
| WO | 2004/070007 | 8/2004 |
| WO | 2004/081183 | 9/2004 |
| WO | WO 2004081183 A2 * | 9/2004 |
| WO | WO2005/090599 | 9/2005 |
| WO | WO2008/015396 | 2/2008 |

OTHER PUBLICATIONS

Skerra, A. Nucleic Acids Research (1992) 20(14): 3551-3554.*
Dietrich et al. FEMS Microbiology Letters (2002) 217: 89-94.*
Gilar et al., "Study of phosphorothioate-modified oligonucleotide resistance to 3'-exonuclease using capillary electrophoresis" Journal of Chromatography B, 714:13-20 (1998).
Griffey et al., 2'-0-Aminopropyl Ribonucleotides: A Zwitterionic Modification that Enhances the Exonuclease Resistance and Biological Activity of Antisense Oligonucleotides, Journal of Medicinal Chemistry, 39:5100-5109 (1996).
Mitra et al., In situ localized amplification and contact replication of many individual DNA molecules, Nucleic Acids Research, 27(24):e34, i-vi (1999).
Adessi, et al., "Solid Phase DNA amplification: characterisation of primer attachment and amplification mechanisms", Nucleic Acids Research 28, 2000, 1-8.
Chenchik, et al., "Full length cDNA cloning", BioTechniques vol. 21, 1996, 526-534.
Gubler, et al., "A simple and very efficient method for generating cDNA Libraries", Gene 25, 1983, 263-269.
Helfman, et al., "Identification of clones that encode chicken tropomyosin by direct immunological screening of a cDNA expression library", PNAS US 80, 1983, 31-35.
Johnson, "Molecular Cloning of DNA from specific chromosomal regions by Microdissection and Sequence-Independent Amplification of DNA", Genomics 6, 1990, 243-251.
Kalisch, et al., "Covalently linked sequencing primer linkers (splinkers) for sequence analysis of restriction fragments", Gene 44, 1986, 263-270.

(Continued)

*Primary Examiner* — Angela M Bertagna
(74) *Attorney, Agent, or Firm* — Brent C. Moore; Illumina, Inc.

(57) ABSTRACT

The invention relates to a method of preparing a library of template polynucleotides which reduces and/or prevents the formation of adaptor-dimers. The invention also relates to the use of a library of templates prepared using the method of the invention for solid-phase nucleic acid amplification. In particular, the invention relates to a method of preparing a library of template polynucleotides which have common sequences at their 5' ends and at their 3' ends which is substantially free of adaptor-dimers.

13 Claims, 3 Drawing Sheets

(56) References Cited

OTHER PUBLICATIONS

Kimmel, et al., "Preparation of cDNA and the Generation of cDNA Libraries: Overview", Methods in Enzymology 152, 1987, 307-316.
Kinzler, et al., "Whole genome PCR: application to the identification of sequences bound by gene regulatory proteins", Nucleic Acids Research, 17(10), 1989, 3645-3653.
Matsuzaki, "Parallel Genotyping of Over 10,000 SNPs Using a One-Primer Assay on a High-Density Oligonucleotide Array", Genome Research, 14, 2004, 414-425.
Mueller, et al., "In Vivo Footprinting of a muscle specific Enhancer by Ligation Mediated PCR", Science 246, 1989, 780-786.
Pfeifer, et al., "Genomic Sequencing and Methylation Analysis by Ligation Mediated PCR", Science 246, 1989, 810-813.
Saiki, et al., "Analysis of enzymatically amplified . . . -globin and HLA-DQ . . . DNA with allele-specific oligonucleotide probes", Nature 324, 1986, 163-166.
Saiki, et al., "Primer-Directed Enzymatic Amplification of DNA with a Thermostable DNA Polymerase", Science 239, 1988, 487-491.
Steigerwald, et al., "Ligation-mediated PCR Improves the sensitivity of methylation analysis by restriction enzymes and detection of specific DNA Strand breaks", Nucleic Acids Research 18, 1990, 1435-1439.
Velculescu, et al., "Serial analysis of gene expression", Science, 270, 1995, 484-487.

* cited by examiner

SEQUENCE LISTING

<160> NUMBER OF SEQ ID NOS: 55

<210> SEQ ID NO 1
<211> LENGTH: 20
<212> TYPE: DNA
<213> ORGANISM: artificial sequence
<220> FEATURE:
<223> OTHER INFORMATION: Synthetic oligonucleotide

<400> SEQUENCE: 1
tggaacagcc gctctcacct                                            20

<210> SEQ ID NO 2
<211> LENGTH: 20
<212> TYPE: DNA
<213> ORGANISM: artificial sequence
<220> FEATURE:
<223> OTHER INFORMATION: Synthetic oligonucleotide

<400> SEQUENCE: 2
tcctggaggg aagtgactat                                            20

<210> SEQ ID NO 3
<211> LENGTH: 33
<212> TYPE: DNA
<213> ORGANISM: artificial sequence
<220> FEATURE:
<223> OTHER INFORMATION: Synthetic oligonucleotide
<220> FEATURE:
<221> NAME/KEY: misc_feature
<222> LOCATION: (32)..(33)
<223> OTHER INFORMATION: Bond between nucleotides 32 and 33 is
      phosphorothioate

<400> SEQUENCE: 3
acactctttc cctacacgac gctcttccga tct                             33

<210> SEQ ID NO 4
<211> LENGTH: 33
<212> TYPE: DNA
<213> ORGANISM: artificial sequence
<220> FEATURE:
<223> OTHER INFORMATION: Synthetic oligonucleotide

<400> SEQUENCE: 4
gatcggaaga gctcgtatgc cgtcttctgc ttg                             33

<210> SEQ ID NO 5
<211> LENGTH: 58
<212> TYPE: DNA
<213> ORGANISM: artificial sequence
<220> FEATURE:
<223> OTHER INFORMATION: Synthetic oligonucleotide
<220> FEATURE:
<221> NAME/KEY: misc_feature
<222> LOCATION: (57)..(58)
<223> OTHER INFORMATION: Bond between nucleotides 57 and 58 is
      phosphorothioate with 2'-OMe modification

<400> SEQUENCE: 5
aatgatacgg cgaccaccga gatctacact ctttccctac acgacgctct tccgatct   58

<210> SEQ ID NO 6
<211> LENGTH: 34
<212> TYPE: DNA
<213> ORGANISM: artificial sequence
<220> FEATURE:
<223> OTHER INFORMATION: Synthetic oligonucleotide

```
<220> FEATURE:
<221> NAME/KEY: misc_feature
<222> LOCATION: (33)..(34)
<223> OTHER INFORMATION: Bond between nucleotides 33 and 34 is
      phosphorothioate with 2'-OMe modification

<400> SEQUENCE: 6
caagcagaag acggcatacg agctcttccg atct                                    34

<210> SEQ ID NO 7
<211> LENGTH: 52
<212> TYPE: DNA
<213> ORGANISM: artificial sequence
<220> FEATURE:
<223> OTHER INFORMATION: Synthetic oligonucleotide

<400> SEQUENCE: 7
aatgatacgg cgaccaccga cactctttcc ctacacgacg ctcttccgat ct                52

<210> SEQ ID NO 8
<211> LENGTH: 34
<212> TYPE: DNA
<213> ORGANISM: artificial sequence
<220> FEATURE:
<223> OTHER INFORMATION: Synthetic oligonucleotide

<400> SEQUENCE: 8
caagcagaag acggcatacg agctcttccg atct                                    34

<210> SEQ ID NO 9
<211> LENGTH: 58
<212> TYPE: DNA
<213> ORGANISM: artificial sequence
<220> FEATURE:
<223> OTHER INFORMATION: Synthetic oligonucleotide
<220> FEATURE:
<221> NAME/KEY: misc_feature
<222> LOCATION: (57)..(58)
<223> OTHER INFORMATION: Bond between nucleotides 57 and 58 is
      phosphorothioate

<400> SEQUENCE: 9
aatgatacgg cgaccaccga gatctacact ctttccctac acgacgctct tccgatct         58

<210> SEQ ID NO 10
<211> LENGTH: 34
<212> TYPE: DNA
<213> ORGANISM: artificial sequence
<220> FEATURE:
<223> OTHER INFORMATION: Synthetic oligonucleotide
<220> FEATURE:
<221> NAME/KEY: misc_feature
<222> LOCATION: (33)..(34)
<223> OTHER INFORMATION: Bond between nucleotides 33 and 34 is
      phosphorothioate

<400> SEQUENCE: 10
caagcagaag acggcatacg agctcttccg atct                                    34

<210> SEQ ID NO 11
<211> LENGTH: 34
<212> TYPE: DNA
<213> ORGANISM: artificial sequence
<220> FEATURE:
<223> OTHER INFORMATION: Synthetic adaptor sequence

<400> SEQUENCE: 11
agatcggaag agctcgtatg ccgtcttctg cttg                                    34
```

<210> SEQ ID NO 12
<211> LENGTH: 20
<212> TYPE: DNA
<213> ORGANISM: artificial sequence
<220> FEATURE:
<223> OTHER INFORMATION: Synthetic oligonucleotide

<400> SEQUENCE: 12
cgaggaactc agcactcatc                                                 20

<210> SEQ ID NO 13
<211> LENGTH: 20
<212> TYPE: DNA
<213> ORGANISM: artificial sequence
<220> FEATURE:
<223> OTHER INFORMATION: Synthetic oligonucleotide

<400> SEQUENCE: 13
atgccgagga agaagccatt                                                 20

<210> SEQ ID NO 14
<211> LENGTH: 44
<212> TYPE: DNA
<213> ORGANISM: artificial sequence
<220> FEATURE:
<223> OTHER INFORMATION: Synthetic oligonucleotide

<400> SEQUENCE: 14
aatgatacgg cgaccaccga gatctacact cttccctac acga                       44

<210> SEQ ID NO 15
<211> LENGTH: 21
<212> TYPE: DNA
<213> ORGANISM: artificial sequence
<220> FEATURE:
<223> OTHER INFORMATION: Synthetic oligonucleotide

<400> SEQUENCE: 15
caagcagaag acggcatacg a                                               21

<210> SEQ ID NO 16
<211> LENGTH: 481
<212> TYPE: DNA
<213> ORGANISM: Homo sapiens

<400> SEQUENCE: 16
caagcagaag acggcatacg agctcttccg atctgctgga gggaaatcca aactcagggg     60
tgcctgtgcc acagcaaaca ctctccctct cacaccacct ggaatagaga tcagctagag    120
cagaggctgc taagagaggg aacagaggct ccttgtgaca gggagactag gatcagaagt    180
cagggaaggg acagccgggt gaaatgactg gaaagaggag caatcactca gcagtaaggc    240
aggttcttcc aaagacaaaa ggacacagag ataagtcagg gcacttccaa ggaacccaac    300
tacctactcc acactcccaa atttattctg ggttgggccc ttttttggttc caatatcacc    360 tcggatacca taacttgtcc aaggtctctt cttacctctc ccaccctaaa tgaagacggg    420
cccagatcgg aagagcgtcg tgtagggaaa gagtgtagat ctcggtggtc gccgtatcat    480
t                                                                   481

<210> SEQ ID NO 17
<211> LENGTH: 298
<212> TYPE: DNA

<213> ORGANISM: Homo sapiens

<400> SEQUENCE: 17

| | | | | |
|---|---|---|---|---|
| atttaaattt | ggggaaccat | tgatggatat | aagtggtatt | taaagccaca ggattaggct | 60 |
| gggcacagtg | gctcatgcct | ataatcccag | ccctttggga | ggctgaggca ggtggatcac | 120 |
| ttgaggccag | gagtttgaga | ccagcctggc | caacatggtg | aaaccctgtc tctaccaaaa | 180 |
| aatacagaaa | attagccgtg | tgtggtggtg | cgtgcctgta | gtcccagata ctcaggaggg | 240 |
| tgaggcagga | gaattgcttg | aatcagatcg | gaagagctcg | tatgccgtct tctgcttg | 298 |

<210> SEQ ID NO 18
<211> LENGTH: 330
<212> TYPE: DNA
<213> ORGANISM: Homo sapiens

<400> SEQUENCE: 18

| | | | | |
|---|---|---|---|---|
| caagcagaag | acggcatacg | agctcttccg | atctggcccc | gccagctctt gtggttgcct | 60 |
| ggaagcatta | tttccatcaa | cactatcccc | agctccacgt | cgtccttttc acctcttttc | 120 |
| ctcgggaccc | ccgcacccca | caggatccta | gtagtggtga | gtgggcaatg agagagggca | 180 |
| acttgggaga | ggtgagttgg | cagggacaa | aggggagaac | agagaggctt attgacaagg | 240 |
| gggcacctgg | tcttgggcct | aagggtggtg | ggagatcgga | agagcgtcgt gtagggaaag | 300 |
| agtgtagatc | tcggtggtcg | ccgtatcatt | | | 330 |

<210> SEQ ID NO 19
<211> LENGTH: 330
<212> TYPE: DNA
<213> ORGANISM: Homo sapiens

<400> SEQUENCE: 19

| | | | | |
|---|---|---|---|---|
| caagcagaag | acggcatacg | agctcttccg | atcttttgcc | atttccacag cagtatgtcc | 60 |
| catccctaga | atatctggca | cctggttaag | tgttcagtac | atatttgttg aatgggtaaa | 120 |
| tgaatgagag | ctggagggaa | atccaaactc | aggggtgcct | gtgccacagc aaacactctc | 180 |
| cctctcacac | cacctggaat | agagatcagc | tagagcagag | gctgctaaga gagggaacag | 240 |
| aggctccttg | tgacagggag | actaggatca | gaagatcgga | agagcgtcgt gtagggaaag | 300 |
| agtgtagatc | tcggtggtcg | ccgtatcatt | | | 330 |

<210> SEQ ID NO 20
<211> LENGTH: 512
<212> TYPE: DNA
<213> ORGANISM: Homo sapiens

<400> SEQUENCE: 20

| | | | | |
|---|---|---|---|---|
| aatgatacgg | cgaccaccga | gatctacact | ctttccctac | acgacgctct tccgatctgc | 60 |
| acaatttcag | ttctatcaag | tttgaaagct | gcaaaattaa | gctgcattgt tgagagatac | 120 |
| acaggtcata | aactaaagag | aaatgtaagg | agttgatttc | cttaaaagga taaagcttgc | 180 |
| atgtatagag | ggagaggatt | atgatcaaga | aggatgagtg | gcggccggta tggtggctca | 240 |
| tccctgtaat | cctagcactt | tgggaggctg | aggcaggcgc | attacttgag gtcaggagtt | 300 |
| tgagaccagc | ctggccaaca | tggcaaaacc | ctatctctac | taaaaataca aaagttagc | 360 |
| caggtgtgga | gccgcacgcc | tgtggtctca | gctactcagg | aggttgaggc acgagaatcg | 420 |
| cttgaacctg | ggaggatgag | gttgtagtga | gccaacatcg | caccactgca ctccagccag | 480 |
| atcggaagag | ctcgtatgcc | gtcttctgct | tg | | 512 |

<210> SEQ ID NO 21
<211> LENGTH: 277
<212> TYPE: DNA
<213> ORGANISM: Homo sapiens

<400> SEQUENCE: 21

```
gatacggcga ccaccgagat ctacactctt tccctacacg acgctcttcc gatctccacc      60
ctgccctgca aaaccaccag ctccgtggtc tctggatggg actcccaggt gcctggggaa     120
ccaaaacaag aaaaaaatgg aggagagttt tgagcaagaa ctaaagccaa ggaaagatgg     180
ggaagaggca aagactagga ataacaataa tctttagagc tgctggcatt cattcattca     240
tccagatcgg aagagctcgt atgccgtctt ctgcttg                              277
```

<210> SEQ ID NO 22
<211> LENGTH: 672
<212> TYPE: DNA
<213> ORGANISM: Homo sapiens

<400> SEQUENCE: 22

```
aatgatacgg cgaccaccga gatctacact ctttccctac acgacgctct tccgatctag      60
aaaatgagat cgctgatggc ttgcagttgg cacgtgaagg aaagtgagga taaagaagga     120
cttccaggtt tttgtcttga caactggaa atactgagat gggaagactg ggggagaagc     180
agatttgaag ctttgggga ggagagggga atcagaaatg aaatttcaga ttctttttaa     240
atatccctag tggagatgtt gaataggcag tgggtaagta gtcagcagct taggggagag     300
aagaggacgg aaatttgaat ttgggaaaga tttaaatttg gggaaccatt gatggatata     360
agtggtatttt aaagccacag gattaggctg ggcacagtgg ctcatgccta taatcccagc     420
cctttgggag gctgaggcag gtggatcact tgaggccagg agtttgagac cagcctggcc     480
aacatggtga aaccctgtct ctaccaaaaa atacagaaaa ttagccgtgt gtggtggtgc     540
gtgcctgtag tcccagatac tcaggagggt gaggcaggag aattgcttga atcctggagg     600
cggaggttac ggtgagccaa gatcatacca ctgcactcag atcggaagag ctcgtatgcc     660
gtcttctgct tg                                                         672
```

<210> SEQ ID NO 23
<211> LENGTH: 542
<212> TYPE: DNA
<213> ORGANISM: Homo sapiens

<400> SEQUENCE: 23

```
aatgatacgg cgaccaccga gatctacact ctttccctac acgacgctct tccgatctgg      60
tgaaaaaagt aggtaagtct tttaaggagt tttcctgcaa agcggacaga gaactaggtc     120
tggtggtggt cgtcaaagga gaactttttt ctccctcctt ccctcccttc ctcctagata     180
cttgcatgtt ttgtaaagag tgagcacagt ggtacatctt ttcttagcca cagtcagctg     240
cccaggagca gtgctgaatg gcagagctg gattttacag ggttgggatt ttgccaggtg     300
agtaagatag aggggagaag tgggaccagg gagttccagg tctgtgaacg gccctggctg     360
aggagctgga tcatgaaatc tgagtcaagt aagaaggaaa ttgaggacac gagttgggta     420
ttgcatagtg ttactgtgtt aaggtcaggg gtcaaagact tactggcatg gagtaaccag     480
agtaagtgag ctggaaagat gagttgtcag atcggaagag ctcgtatgcc gtcttctgct     540
tg                                                                    542
```

<210> SEQ ID NO 24
<211> LENGTH: 281
<212> TYPE: DNA
<213> ORGANISM: Homo sapiens

<400> SEQUENCE: 24

| | | | | | |
|---|---|---|---|---|---|
| caagcagaag | acggcatacg | agctcttccg | atctcaggga | ggaggtagag | aggagaaaga | 60 |
| gagcagcccg | ggagcaagtt | ctacagccgg | tcagtgctga | gttgttggag | ctggacatcc | 120 |
| gggaggtgta | tcagcctggc | tcaggtgagt | gagagcaaga | caggcattgg | gctggggaag | 180 |
| gagtttggaa | aggtaaaagc | cgactgtgag | gaaggagggg | tctagatcgg | aagagcgtcg | 240 |
| tgtagggaaa | gagtgtagat | ctcggtggtc | gccgtatcat | t | | 281 |

<210> SEQ ID NO 25
<211> LENGTH: 629
<212> TYPE: DNA
<213> ORGANISM: Homo sapiens

<400> SEQUENCE: 25

| | | | | | |
|---|---|---|---|---|---|
| caagcagaag | acggcatacg | agctcttccg | atcttggaac | agccgctctc | acctcagttc | 60 |
| atctggggaa | gggctacaa | agcaaacaat | ctttattcac | aattggggtg | gcagagggga | 120 |
| gataccccca | ggtcagtcca | aaagcaaaga | tactgggagg | gaagatggcg | ctgggcgagg | 180 |
| aactcagcac | tcatcctcac | ccagcagggc | ataaggtttt | cggccagcca | ggctggaccc | 240 |
| tggagccgag | gttggggtct | cctcatcccc | ttctccctcc | tcatccgcat | ccggtcctc | 300 |
| ctctcccctcc | tcctcacagg | agctgctcag | ctcttcctct | tcctccacct | cctcgtcacc | 360 |
| tgctggcccc | accctgccct | gcaaaaccac | cagctccgtg | gtctctggat | gggactccca | 420 |
| ggtgcctggg | gaaccaaaac | aagaaaaaaa | tggaggagag | ttttgagcaa | gaactaaagc | 480 |
| caaggaaaga | tggggaagag | gcaaagacta | ggaataacaa | taatctttag | agctgctggc | 540 |
| attcattcat | tcatccattc | attcaacttc | cagatcggaa | gagcgtcgtg | tagggaaaga | 600 |
| gtgtagatct | cggtggtcgc | cgtatcatt | | | | 629 |

<210> SEQ ID NO 26
<211> LENGTH: 574
<212> TYPE: DNA
<213> ORGANISM: Homo sapiens

<400> SEQUENCE: 26

| | | | | | |
|---|---|---|---|---|---|
| caagcagaag | acggcatacg | agctcttccg | atcttggagt | gcagtggcac | aatcatagct | 60 |
| cactgcagcc | ttgaactctt | gggctcaagt | gatcctcctg | cctcagcctc | tgaagtagca | 120 |
| gagactacag | gcacatacca | ccacacttgg | ctagttttct | ttatcttttg | taaagatggg | 180 |
| gtttcactat | gttgcccaca | ctagtcttga | gctcctggtc | tcaagcaatc | ctcccacctc | 240 |
| agcctcccaa | agcgctggga | ctatataggc | atgagccctc | acacatggcc | gtcatccatt | 300 |
| cttttactca | ggtatcaatg | tccttatttt | taaaatcaaa | gtaactaaga | ctcagagtag | 360 |
| caaaatcact | tactcaagac | ctcacagctg | agaagaggtg | gaatttaact | caggctgtca | 420 |
| tgatccttcc | actgcagcag | acgcctcttc | tgccttgccc | accgccactg | gcagagatca | 480 |
| ccctcagac | accctggggc | ctaatgagac | ctgatcgaga | tcggaagagc | gtcgtgtagg | 540 |
| gaaagagtgt | agactcggtg | gtcgccgtat | catt | | | 574 |

<210> SEQ ID NO 27
<211> LENGTH: 531

<212> TYPE: DNA
<213> ORGANISM: Homo sapiens

<400> SEQUENCE: 27

```
caagcagaag acggcatacg agctcttccg atctctcgcc ttttacccct ccctgtctcc      60
tttcctctcc tcagagattc tgccattgat gaagctgctg tccactcacc cctagatttt     120
tgttgcatag ccagtaagat ctctggcctg gaatgttttg gggaaaactg aaggactgt      180
gttatgggag tggagtata actggtacct ggttaatgct ttccctttcc attattcttt      240
tcttcctcca gcctgggcag agaaacgtgg ttacaagaca gccaaggcgg ctcggaatga     300
tgtgtacaga gcagccaaca gtctcttgcg gctggcagtg gacggccgcc tcagcctgtg     360
ttttcatccc ccaggctaca gtgaacagaa aggtcagagc ccagatattc ttccccagcc     420
ccctgctata gcgtaggtaa aagggtgtgg gctttgtggc cagagagagg gtcagatcgg     480
aagagcgtcg tgtagggaaa gagtgtagat ctcggtggtc gccgtatcat t              531
```

<210> SEQ ID NO 28
<211> LENGTH: 573
<212> TYPE: DNA
<213> ORGANISM: Homo sapiens

<400> SEQUENCE: 28

```
caagcagaag acggcatacg agctcttccg atctaggaaa gtgaggataa agaaggactt      60
ccaggttttt gtcttgagca actggaaata ctgagatggg aagactgggg gagaagcaga     120
tttgaaggct ttggggagga gaggggaatc agaaatgaaa tttcagattc ttttttaaata    180
tccctagtgg agatgttgaa taggcagtgg gtaagtagtc agcagcttag gggagagaag     240
aggacggaaa tttgaatttg ggaaagattt aaatttgggg aaccattgat ggatataagt     300
ggtatttaaa gccacaggat taggctgggc acagtggctc atgcctataa tcccagccct     360
ttgggaggct gaggcaggtg gatcacttga ggccaggagt ttgagaccag cctggccaac     420
atggtgaaac cctgtctcta ccaaaaaata cagaaaatta gccgtgtgtg gtgatgcgtg     480
cctgtagtcc cagatactca ggagggtgag gcaggagatc ggaagagcgt cgtgtaggga     540
aagagtgtag atctcggtgg tcgccgtatc att                                  573
```

<210> SEQ ID NO 29
<211> LENGTH: 311
<212> TYPE: DNA
<213> ORGANISM: Homo sapiens

<400> SEQUENCE: 29

```
caagcagaag acggcatacg agctcttccg atctgggctg gtggggcgga aagtcgtgag      60
tgtctccaga accccgggcc atacccgata ctttcagacc tactttctta ccccctctgt     120
gaagctctgt gactgcccag gcctcatctt cccatctctt ctgcctaggc agttgcaggt     180
atgacgggga gggtgggtaa gggaaagaga gaaggtggga cattgaggaa agtactgagt     240
gctcatttcc ctcagatcgg aagagcgtcg tgtagggaaa gagtgtagat ctcggtggtc     300
gccgtatcat t                                                          311
```

<210> SEQ ID NO 30
<211> LENGTH: 416
<212> TYPE: DNA
<213> ORGANISM: Homo sapiens

<400> SEQUENCE: 30

```
caagcagaag acggcatacg agctcttccg atctcacgcc tgtggtctca gctactcagg    60
aggttgaggc acgagaatcg cttgaacctg ggaggatgag gttgtagtga gccaacatcg   120
caccactgca ctccagcccg ggtgagggag tgagactctg tctcaaaaac aaaaacaaaa   180
aaaaacaagg acagatggaa catgttgtca cacattgggt ggtatggggt tcatcaggct   240
gcacatgtat gttctgtgca ttttttttgta tgttgtagtt tacagttaca agaagatag   300
caggaagaaa tggtgaaaaa agtaggtaag tcttttaagg agttttcctg caaagcggag   360
atcggaagag cgtcgtgtag ggaaagagtg tagatctcgg tggtcgccgt atcatt       416
```

```
<210> SEQ ID NO 31
<211> LENGTH: 548
<212> TYPE: DNA
<213> ORGANISM: Homo sapiens

<400> SEQUENCE: 31
```

```
gatacggcga ccaccgagat ctacactctt tccctacacg acgctcttcc gatcttggaa    60
cagccgctct cacctcagtt catctgggga aggggctaca aagcaaacaa tctttattca   120
caattgggt ggcagagggg agatacccc aggtcagtcc aaaagcaaag atactgggag     180
ggaagatggc gctgggcgag gaactcagca ctcatcctca cccagcaggg cataagggtt   240
tcggccagcc aggctggacc ctggagccga ggttggggtc tcctcatccc cttctccctc   300
ctcatccgca tccggtcct cctctcccctc ctcctcacag gagctgctca gctcttcctc    360
ttcctcctcc tcctcgtcac ctgctggccc caccctgccc tgcaaaacca ccagctccgt   420
ggtctctgga tgggactccc aggtgcctgg ggaaccaaaa caagaaaaaa atggaggaga   480
gttttgagca agaactaaag ccaaggaaag atggagatcg aagagctcg tatgccgtct    540
tctgcttg                                                             548
```

```
<210> SEQ ID NO 32
<211> LENGTH: 654
<212> TYPE: DNA
<213> ORGANISM: Homo sapiens

<400> SEQUENCE: 32
```

```
aatgatacgg cgaccaccga gatctacact ctttccctac acgacgctct tccgatctag    60
agaaaggaaa tagttggaga agaggaggtc aaggactgag ccttaggaca agccagcatt   120
tagttgggca aaggacagtg agaaggagga aaaccaaggg agcgtcccag aagtcaaatg   180
aagaaggtgt ttgaagagga aaggaggaat cagctgtgtc aactgttgct gacaggccaa   240
atgagagaac agagagctgc tcagcaggct tggcaatgtg aagatccgtg gtttcagtgg   300
ggtggagaaa gccaaactgg agtaggccca tgagagaagg tgcaacaact tcacataaca   360
ttgtgtgaaa agagtctgac ccaatagcat ccatactgca caatttcagt tctatcaagt   420
ttgaaagctg caaaattaag ctgcattgtt gagagataca caggtcataa actaaagaga   480
aatgtaagga gttgatttcc ttaaaaggat aaagcttgca tgtatagagg gagaggatta   540
tgatcaagaa ggatgagtgg cggccggtat ggtggctcat ccctgtaatc ctagcacttt   600
gggaggctga ggcaggcgca agatcggaag agctcgtatg ccgtcttctg cttg         654
```

```
<210> SEQ ID NO 33
<211> LENGTH: 436
<212> TYPE: DNA
<213> ORGANISM: Homo sapiens

<400> SEQUENCE: 33
```

```
caagcagaag acggcatacg agctcttccg atctgggatg aggtcagcaa gatcaccagg      60
gcccacatca tgtagagccc tgaggctgtg acagccattt tggattttat tccaagtctc     120
atgagaagcc aagggtaggt tttgaacagg ggaatgatag gatctgattt tgtttcttat     180
aagtttacct cctgagtaga gaataaatga tgggggtgg gcaagaaagg gagcagagag      240
agcagttgag gctatttcag taatctagga gagaaataag agttgcttag agtaggatgc     300
tggagctgga ggtggtgaga cagggccgga agcatgatat attttgaagg tagagaaaat     360
gagatcgctg atggcttgag atcggaagag cgtcgtgtag ggaaagagtg tagatctcgg     420
tggtcgccgt atcatt                                                    436

<210> SEQ ID NO 34
<211> LENGTH: 440
<212> TYPE: DNA
<213> ORGANISM: Homo sapiens

<400> SEQUENCE: 34
aatgatacgg cgaccaccga gatctacact ctttccctac acgacgctct tccgatctgg      60
gaggactgaa catcggaaga agttgagtgg gatgaaaggg agtcaggccg atgggggaga    120
gggtcttatg gccctgaga gctggccagc actggcgtca ccggcccctc cccgcagggc     180
ttcaagatgg gctgcgctcc agttccaaca gccgcagcgg gagccgggag cggcgagagg    240
aacagaccga cacctcggac ggggagtctg tgacccatca tatccgcagg cttaaccagc    300
agccttctca ggggctgggt ccacgaggct acgacccaaa tcggtgaggg tgggaggggg    360
cgctggtccc ggctttcccg cctacccgga agtcagagct ttggggagat cggaagagct    420
cgtatgccgt cttctgcttg                                                440

<210> SEQ ID NO 35
<211> LENGTH: 541
<212> TYPE: DNA
<213> ORGANISM: Homo sapiens

<400> SEQUENCE: 35
aatgatacgg cgaccaccga gatctacact ctttccctac acgacgctct tccgatctcg      60
acccaaatcg gtgagggtgg gaggggggcgc tggtcccggc tttccgcct acccggaagt    120 cagagctttg ggggaaagcg ggctgctact ggtgaagacg gtgggcctgg gatgccacag    180
ttctccgcta gccactcggc tccccacagc gggccacagt cttcctttcc agaggggctg    240
gagagagttg ggcttttaga aggagaaggc tgagtattgc ctgaaagaag gacttggggg    300
aagtctgact tgagagagga gacttgaacg actctggaga gaatggtttg cgaagttgat    360
tgtacaagag gggagaaaat aggagtttgt ggccacagga ttgctctgga tgtctcggtc    420
cctgttccct tagataccga ctgcattttg agagagacag cagggaggag gtagagagga    480
gaaagagagc agcccgggag caagttcaga tcggaagagc tcgtatgccg tcttctgctt    540
g                                                                    541

<210> SEQ ID NO 36
<211> LENGTH: 813
<212> TYPE: DNA
<213> ORGANISM: Homo sapiens

<400> SEQUENCE: 36
aatgatacgg cgaccaccga gatctacact ctttccctac acgacgctct tccgatctgc      60
```

```
cgtgtgtggt ggtgcgtgcc tgtagtccca gatactcagg agggtgaggc aggagaattg      120
cttgaatcct ggaggcggag gttacggtga gccaagatca taccactgca ctccagcctg      180
ggtgacagag caagacttcg tcaaaaaaaa aaaaaaaaaa gccatggaat tggatgagat      240
gtaggagaga aaggaaatag ttggagaaga ggaggtcaag gactgagcct taggacaagc      300
cagcatttag ttgggcaaag gacagtgaga aggaggaaaa ccaagggagc gtcccagaag      360
tcaaatgaag aaggtgtttg aagaggaaag gaggaatcag ctgtgtcaac tgttgctgac      420
aggccaaatg agagaacaga gagctgctca gcaggcttgg caatgtgaag atccgtggtt      480
tcagtggggt ggagaaagcc aaactggagt aggcccatga gagaaggtgc aacaacttca      540
cataacattg tgtgaaaaga gtctgaccca atagcatcca tactgcacaa tttcagttct      600
atcaagtttg aaagctgcaa aattaagctg cattgttgag agatacacag gtcataaact      660
aaagagaaat gtaaggagtt gatttcctta aaaggataaa gcttgcatgt atagagggag      720
aggattatga tcaagaagga tgagtggcgg ccggtatggt ggctcatccc tgtaatccta      780
gatcggaaga gctcgtatgc cgtcttctgc ttg                                  813
```

<210> SEQ ID NO 37
<211> LENGTH: 190
<212> TYPE: DNA
<213> ORGANISM: Homo sapiens

<400> SEQUENCE: 37

```
caagcagaag acggcatacg agctcttccg atctgtggtg agtgagcaga gtggcagtga       60
gccccaaggc ttccagtttt ctccttggac aagtcatcgt aattattatt attatttttt      120
gagatggagt ttagatcgga agagcgtcgt gtagggaaag agtgtagatc tcggtggtcg      180
ccgtatcatt                                                            190
```

<210> SEQ ID NO 38
<211> LENGTH: 166
<212> TYPE: DNA
<213> ORGANISM: Homo sapiens

<400> SEQUENCE: 38

```
aatgatacgg cgaccaccga gatctacact ctttccctac acgacgctct tccgatctaa       60
aacctaccct tggcttctca tgagacttgg aataaaatcc aaaatggctg tcacagcctc      120
agggctctac atagatcgga gagctcgta tgccgtcttc tgcttg                     166
```

<210> SEQ ID NO 39
<211> LENGTH: 204
<212> TYPE: DNA
<213> ORGANISM: Homo sapiens

<400> SEQUENCE: 39

```
caagcagaag acggcatacg agctcttccg atctgatagg atctgatttt gtttcttata       60
agtttacctc ctgagtagag aataaatgat ggggggtggg caagaaaggg agcagagaga      120
gcagttgagg ctatttcagt aatctaggag atcggaagag cgtcgtgtag ggaaagagtg      180
tagatctcgg tggtcgccgt atca                                            204
```

<210> SEQ ID NO 40
<211> LENGTH: 138
<212> TYPE: DNA
<213> ORGANISM: Homo sapiens

<400> SEQUENCE: 40

```
caagcagaag acggcatacg agctcttccg atctccagca ggtgacgagg aggaggagga    60
agaggaagag ctgagcagct ccagatcgga agagcgtcgt gtagggaaag agtgtagatc   120
tcggtggtcg ccgtatca                                                 138

<210> SEQ ID NO 41
<211> LENGTH: 162
<212> TYPE: DNA
<213> ORGANISM: Homo sapiens

<400> SEQUENCE: 41
caagcagaag acggcatacg agctcttccg atctgagagc agttgaggct atttcagtaa    60
tctaggagag aaataagagt tgcttagagt aggatgctgg agctagatcg gaagagcgtc   120
gtgtagggaa agagtgtaga tctcggtggt cgccgtatca tt                      162

<210> SEQ ID NO 42
<211> LENGTH: 168
<212> TYPE: DNA
<213> ORGANISM: Homo sapiens

<400> SEQUENCE: 42
caagcagaag acggcatacg agctcttccg atctctccca ccctcaccga tttgggtcgt    60
agcctcgtgg acccagcccc tgagaaggct gctggttaag cctgcggata tgagatcgga   120
agagcgtcgt gtagggaaag agtgtagatc tcggtggtcg ccgtatca                168

<210> SEQ ID NO 43
<211> LENGTH: 155
<212> TYPE: DNA
<213> ORGANISM: Homo sapiens

<400> SEQUENCE: 43
caagcagaag acggcatacg agctcttccg atctaggtga gtgagagcaa gacaggcatt    60
gggctgggga aggagtttgg aaaggtaaaa gccgactaga tcggaagagc gtcgtgtagg   120
gaaagagtgt agatctcggt ggtcgccgta tcatt                              155

<210> SEQ ID NO 44
<211> LENGTH: 582
<212> TYPE: DNA
<213> ORGANISM: Homo sapiens

<400> SEQUENCE: 44
aatgatacgg cgaccaccga gatctacact ctttccctac acgacgctct tccgatcttg    60
cactccagcc cgggtgaggg agtgagactc tgtctcaaaa acaaaaacaa aaaaaaacaa   120
ggacagatga acatgttgt cacacattgg gtggtatggg gttcatcagg ctgcacatgt    180
atgttctgtg cattttttg tatgttgtag tttacagtta caaagaagat agcaggaaga   240
aatggtgaaa aaagtaggta agtctttaa ggagttttcc tgcaaagcgg acagagaact    300
aggtctggtg gtggtcgtca aggagaact tttttctccc tccttccctc ccttcctcct   360
agatacttgc atgtgttgta aagagtgagc acagtggtac atcttttctt agccacagtc   420
agctgcccag gagcagtgct gaatgggcag agctggattt tacagggttg ggattttgcc   480
aggtgagtaa gatagagggg agaagtggga ccagggagtt ccaggtctgt gaacggccct   540
ggctgaggag atcggaagag ctcgtatgcc gtcttctgct tg                      582

<210> SEQ ID NO 45
```

<211> LENGTH: 157
<212> TYPE: DNA
<213> ORGANISM: Homo sapiens

<400> SEQUENCE: 45

| caagcagaag acggcatacg agctcttccg atctgaagct cagagaaacg tgcgtgattc | 60 |
| cagggagggt agggtcaaat gacttttggg agattctcta gatcggaaga gcgtcgtgta | 120 |
| gggaaagagt gtagatctcg gtggtcgccg tatcatt | 157 |

<210> SEQ ID NO 46
<211> LENGTH: 159
<212> TYPE: DNA
<213> ORGANISM: Homo sapiens

<400> SEQUENCE: 46

| caagcagaag acggcatacg agctcttccg atctggaaat tcacaaccta ggacagagtt | 60 |
| gataagagga tggagcagtg aaagtcaacc cagagttctc tagatcggaa gagcgtcgtg | 120 |
| tagggaaaga gtgtagatct cggtggtcgc cgtatcatt | 159 |

<210> SEQ ID NO 47
<211> LENGTH: 161
<212> TYPE: DNA
<213> ORGANISM: Homo sapiens

<400> SEQUENCE: 47

| caagcagaag acggcatacg agctcttccg atctaataag agttgcttag agtaggatgc | 60 |
| tggagctgga ggtggtgaga cagggccgga agcatgatat attagatcgg aagagcgtcg | 120 |
| tgtagggaaa gagtgtagat ctcggtggtc gccgtatcat t | 161 |

<210> SEQ ID NO 48
<211> LENGTH: 162
<212> TYPE: DNA
<213> ORGANISM: Homo sapiens

<400> SEQUENCE: 48

| aatgatacgg cgaccaccga gatctacact ctttccctac acgacgctct tccgatctcg | 60 |
| tgtgtggtgg tgcgtgcctg tagtcccaga tactcaggag ggtgaggcag gagaattgct | 120 |
| tgaatcctag atcggaagag ctcgtatgcc gtcttctgct tg | 162 |

<210> SEQ ID NO 49
<211> LENGTH: 202
<212> TYPE: DNA
<213> ORGANISM: Homo sapiens

<400> SEQUENCE: 49

| caagcagaag acggcatacg agctcttccg atctaaagca atgaaagggg atagagagtg | 60 |
| actgagagga gaggtgctca gggaaaacct ccctgaggag agaactggat gatgagatga | 120 |
| agtgagccat tcagaactgt ggggagatcg gaagagcgtc gtgtagggaa agagtgtaga | 180 |
| tctcggtggt cgccgtatca tt | 202 |

<210> SEQ ID NO 50
<211> LENGTH: 167
<212> TYPE: DNA
<213> ORGANISM: Homo sapiens

<400> SEQUENCE: 50

| caagcagaag acggcatacg agctcttccg atcttaaaag gataaagctt gcatgtatag | 60 |

```
agggagagga ttatgatcaa gaaggatgag tggcggccgg tatggtggca gatcggaaga      120
gcgtcgtgta gggaaagagt gtagatctcg gtggtcgccg tatcatt                   167

<210> SEQ ID NO 51
<211> LENGTH: 173
<212> TYPE: DNA
<213> ORGANISM: Homo sapiens

<400> SEQUENCE: 51
caagcagaag acggcatacg agctcttccg atctctgaga tgggaagact gggggagaag      60
cagatttgaa ggctttgggg aggagagggg aatcagaaat gaaatttcag attctagatc     120
ggaagagcgt cgtgtaggga aagagtgtag atctcggtgg tcgccgtatc att            173

<210> SEQ ID NO 52
<211> LENGTH: 169
<212> TYPE: DNA
<213> ORGANISM: Homo sapiens

<400> SEQUENCE: 52
aatgatacgg cgaccaccga gatctacact ctttccctac acgacgctct tccgatctga     60
gaggtgagtt ggcaggggac aaaggggaga acagagaggc ttattgacaa gggggcacct    120
ggtcttgggc ctaagagatc ggaagagctc gtatgccgtc ttctgcttg                 169

<210> SEQ ID NO 53
<211> LENGTH: 159
<212> TYPE: DNA
<213> ORGANISM: Homo sapiens

<400> SEQUENCE: 53
caagcagaag acggcatacg agctcttccg atctcaagaa agggagcaga gagagcagtt    60 gaggctatt cagtaatcta ggagagaaat aagagttgct tagagtagga tagatcggaa    120
gagcgtcgtg tagggaaaga gtgtagatct cggtggtcg                           159

<210> SEQ ID NO 54
<211> LENGTH: 147
<212> TYPE: DNA
<213> ORGANISM: Homo sapiens

<400> SEQUENCE: 54
aatgatacgg cgaccaccga gatctacact ctttccctac acgacgctct tccgatctaa    60
agcttgcatg tatagaggga gaggattatg atcaagaagg atgagtggcg gccagatcgg    120
aagagctcgt atgccgtctt ctgcttg                                        147

<210> SEQ ID NO 55
<211> LENGTH: 173
<212> TYPE: DNA
<213> ORGANISM: Homo sapiens

<400> SEQUENCE: 55
caagcagaag acggcatacg agctcttccg atcttctacc aaaaaataca gaaaattagc    60
cgtgtgtggt ggtgcgtgcc tgtagtccca gatactcagg agggtgaggc aggagagatc    120
ggaagagcgt cgtgtaggga aagagtgtag atctcggtgg tcgccgtatc att           173
```

METHOD OF LIBRARY PREPARATION AVOIDING THE FORMATION OF ADAPTOR DIMERS

CROSS REFERENCE TO RELATED APPLICATIONS

The present application is a National Stage Application claiming the priority of co-pending PCT Application No. PCT/GB2007/002865, filed Jul. 30, 2007, which in turn, claims priority from U.S. Provisional Application Ser. No. 60/834,424, filed Jul. 31, 2006. Applicants claim priority under 35 U.S.C. §119 as to said U.S. Provisional application, and the entire disclosure of which application is incorporated by reference in its entirety.

FIELD OF THE INVENTION

The invention relates to a method of preparing a library of template polynucleotides which reduces and/or prevents the formation of adaptor-dimers. The invention also relates to the use of a library of templates prepared using the method of the invention for solid-phase nucleic acid amplification. In particular, the invention relates to a method of preparing a library of template polynucleotides which have common sequences at their 5' ends and at their 3' ends which is substantially free of adaptor dimers.

BACKGROUND OF THE INVENTION

Several publications and patent documents are referenced in this application in order to more fully describe the state of the art to which this invention pertains. The disclosure of each of these publications and documents is incorporated by reference herein.

The ability to acquire and analyse DNA sequence data has increased phenomenally over the past few years. As a result nucleic acid analysis has become increasingly important in many areas of biology, biotechnology and medicine. Molecular biology and pharmaceutical drug development now make intensive use of nucleic acid analysis. The most challenging areas are whole genome sequencing, single nucleotide polymorphism detection, screening and gene expression monitoring, which typically require generation and analysis of large amounts of nucleic acid sequence data.

One area of technology which revolutionised the study of nucleic acids was the development of nucleic acid amplification techniques, such as the polymerase chain reaction (PCR). Amplification reactions, such as PCR, can enable the user to specifically and selectively amplify a particular target nucleic acid of interest from a complex mixture of nucleic acids. However, there is also an ongoing need for nucleic acid amplification techniques which enable simultaneous amplification of complex mixtures of templates of diverse sequence, such as genomic DNA fragments (e.g. 'whole genome' amplification) or cDNA libraries, in a single amplification reaction.

PCR amplification cannot occur in the absence of annealing of forward and reverse amplification primers to primer binding sequences in the template to be amplified under the conditions of the annealing steps of the PCR reaction, i.e. if there is insufficient complementarity between primers and template. Some prior knowledge of the sequence of the template is therefore required before one can carry out a PCR reaction to amplify a specific template, unless random primers are used with a consequential loss of specificity. The user must usually know the sequence of at least the primer-binding sites in the template in advance so that appropriate primers can be designed, although the remaining sequence of the template may be unknown. The need for prior knowledge of the sequence of the template increases the complexity and cost of PCR amplification of complex mixtures of templates, such as genomic DNA fragments.

Several of the new methods employed for high throughput DNA sequencing (*Nature*. 437, 376-380 (2005); *Science*. 309, 5741, 1728-1732 (2005)) rely on a universal amplification reaction, whereby a DNA sample is randomly fragmented, then treated such the ends of the different fragments all contain the same DNA sequence. Fragments with universal ends can be amplified in a single reaction with a single pair of amplification primers. Separation of the library of fragments to the single molecule level prior to amplification ensures that the amplified molecules form discrete populations, that can then be further analysed. Such separations can be performed either in emulsions (*Nature*. 437, 376-380 (2005); *Science*. 309, 5741, 1728-1732 (2005)), or on a surface (Nucleic Acids Research 27, e34 (1999); Nucleic Acids Research 15, e87 (2000)).

WO 98/44151 and WO 00/18957 both describe methods of forming polynucleotide arrays based on 'solid-phase' nucleic acid amplification, which is a bridging amplification reaction wherein the amplification products are immobilised on a solid support in order to form arrays comprised of nucleic acid clusters or 'colonies'. Each cluster or colony on such an array is formed from a plurality of identical immobilised polynucleotide strands and a plurality of identical immobilised complementary polynucleotide strands. The arrays so-formed are generally referred to herein as 'clustered arrays' and their general features will be further understood by reference to WO 98/44151 or WO 00/18957, the contents of both documents being incorporated herein in their entirety by reference.

In common with all amplification techniques, solid-phase bridging amplification requires the use of forward and reverse amplification primers which include 'template-specific' nucleotide sequences which are capable of annealing to sequences in the template to be amplified, or the complement thereof, under the conditions of the annealing steps of the amplification reaction. The sequences in the template to which the primers anneal under conditions of the amplification reaction may be referred to herein as 'primer-binding' sequences.

Certain embodiments of the methods described in WO 98/44151 and WO 00/18957 make use of 'universal' primers to amplify templates comprising a variable template portion that it is desired to amplify flanked 5' and 3' by common or 'universal' primer binding sequences. The 'universal' forward and reverse primers include sequences capable of annealing to the 'universal' primer binding sequences in the template construct. The variable template portion, or 'target' may itself be of known, unknown or partially known sequence. This approach has the advantage that it is not necessary to design a specific pair of primers for each target sequence to be amplified; the same primers can be used for amplification of different templates provided that each template is modified by addition of the same universal primer-binding sequences to its 5' and 3' ends. The variable target sequence can therefore be any DNA fragment of interest. An analogous approach can be used to amplify a mixture of templates (targets with known ends), such as a plurality or library of target nucleic acid molecules (e.g. genomic DNA fragments), using a single pair of universal forward and reverse primers, provided that each template molecule in the mixture is modified by the addition of the same universal primer-binding sequences.

Such 'universal primer' approaches to PCR amplification, and in particular solid-phase bridging amplification, are advantageous since they enable multiple template molecules of the same or different, known or unknown sequence to be amplified in a single amplification reaction, which may be carried out on a solid support bearing a single pair of 'universal' primers. Simultaneous amplification of a mixture of templates of different sequences would otherwise require a plurality of primer pairs, each pair being complementary to each unique template in the mixture. The generation of a plurality of primer pairs for each individual template is not a viable option for complex mixtures of templates.

The addition of universal priming sequences onto the ends of targets to be amplified by PCR can be achieved by a variety of methods known to those skilled in the art. For example, a universal primer consisting of a universal sequence at its 5' end and a degenerate sequence at its 3' end can be used in a PCR (DOP-PCR, eg PNAS 1996 vol 93 pg 14676-14679) to amplify fragments randomly from a complex target sequence or a complex mixture of target sequences. The degenerate 3' portion of the primer anneals at random positions on DNA and can be extended to generate a copy of the target that has the universal sequence at its 5' end.

Alternatively, adaptors that contain universal priming sequences can be ligated onto the ends of the target sequences. The adaptors may be single-stranded or double-stranded. If double-stranded, they may have overhanging ends that are complementary to overhanging ends on the target molecules that may have been generated with a restriction endonuclease, or added with a DNA polymerase or terminal transferase. Alternatively, the double-stranded adaptors may be blunt, in which case the targets are also blunt ended. The blunt ends of the targets may have been formed during a process to shear the DNA into fragments, or they may have been formed by an end repair reaction, as would be well known to those skilled in the art.

A single adaptor or two different adaptors may be used in a ligation reaction with target sequences. If a target has been manipulated such that its ends are the same, i.e. both are blunt or both have the same overhang, then ligation of a single compatible adaptor will generate a template with that adaptor on both ends. However, if two compatible adaptors, adaptor A and adaptor B, are used, then three permutations of ligated products are formed: template with adaptor A on both ends, template with adaptor B on both ends, and template with adaptor A on one end and adaptor B on the other end. This last product is, under some circumstances, the only desired product from the ligation reaction and consequently additional purification steps are necessary following the ligation reaction to purify it from the ligation products that have the same adaptor at both ends.

A major drawback in preparing nucleic acid fragment libraries by ligating adaptors to the ends of template nucleic acid fragments is the formation of adaptor-dimers. Adaptor-dimers are formed by the ligation of two adaptors directly to each other such that they do not contain a template nucleic acid fragment as an insert. Such molecules are undesirable, in that during any amplification steps, for example during a universal amplification reaction, adaptor-dimers are amplified alongside the nucleic acid fragment library. Since adaptor-dimers are generally smaller than the fragments contained in the libraries they amplify and accumulate at a faster rate. This reduces the efficiency of the amplification reaction by limiting amplification of the library fragments by depletion of components, such as for example dNTP's and primers, in the amplification reaction. Another more serious concern that when such amplified fragments are sequenced they do not give useful sequence information since they contain no insert. In the case of clustered arrays, a significant population of clusters that have no target DNA sequence is undesirable due to the lower density of real sequence data obtained from a chip of finite size. Hence the efficiency of sequencing can be significantly reduced. Thus, the preparation of libraries with a low level of adaptor-dimers is highly advantageous in the sequencing of polynucleotides, particularly when such processes are high-throughput.

The invention presented herein is directed to a method of generating a library of template polynucleotides using a single adaptor construct in a ligation reaction which reduces and/or prevents the formation of adaptor-dimers. The method can be applied to preparing simple or complex populations of templates for amplification, for example on a solid surface, using primer sequences, with no prior knowledge of the target sequences. The invention is applicable to the preparation of templates from complex samples such as whole genomes or mixtures of cDNAs, as well as mono-template applications.

SUMMARY OF THE INVENTION

A first aspect of the invention provides a method for generating a library of template polynucleotide molecules from one or more primary polynucleotide molecules; said method comprising:
(a) fragmenting said one or more primary polynucleotide molecules to produce target polynucleotide duplexes;
(b) ligating an adaptor polynucleotide construct to both ends of the target polynucleotide duplexes to form combined ligated adaptor-target-adaptor sequences;
(c) preparing an amplification reaction comprising said combined ligated adaptor-target-adaptor sequences and at least two different primer oligonucleotides wherein said primer oligonucleotides are complementary to both a part of the adaptor polynucleotide sequence portion of the combined ligated adaptor-target-adaptor sequences, and complementary to at least one base of either the target polynucleotide duplexes, or an overhang attached to the target duplex;
(d) carrying out an amplification reaction in which said at least two different primer oligonucleotides are annealed to complementary parts of the adaptor-target-adaptor sequence and extended by sequential addition of nucleotides to generate amplification products complementary to at least one strand of the combined ligated adaptor-target-adaptor sequences, wherein said amplification products have a first common sequence at their 5' ends and a second common sequence at their 3' ends and collectively provide a library of template polynucleotide molecules. See FIG. 1 for schematic representation.

A second aspect of the invention provides a method for generating a library of template polynucleotide molecules from one or more primary polynucleotide molecules; said method comprising:
(a) fragmenting said one or more primary polynucleotide molecules to produce target polynucleotide duplexes;
(b) ligating an adaptor polynucleotide construct to both ends of the target polynucleotide duplexes to form combined ligated adaptor-target-adaptor sequences; wherein said adaptor polynucleotide construct contains at least one overhanging base that is modified such that the nucleic acid strand is resistant to exonucleolysis;
(c) preparing an amplification reaction comprising said combined ligated adaptor-target-adaptor sequences and at least two different primer oligonucleotides wherein said primer oligonucleotides are complementary to a part of the adaptor polynucleotide sequence portion of the combined ligated adaptor-target-adaptor sequences;
(d) carrying out an amplification reaction in which said at least two different primer oligonucleotides are annealed to complementary parts of the adaptor-target-adaptor sequence and extended by sequential addition of nucleotides to generate amplification products complementary to at least one strand of the combined ligated adaptor-target-adaptor sequences and wherein said amplification products have a common sequence at their 5' ends and a common sequence at their 3' ends and collectively provide a library of template polynucleotide molecules.

A third aspect of the invention combines the first and second aspects, and provides a method for generating a library of template polynucleotide molecules from one or more primary polynucleotide molecules; said method comprising:
(a) fragmenting said one or more primary polynucleotide molecules to produce target polynucleotide duplexes;
(b) ligating an adaptor polynucleotide construct to both ends of the target polynucleotide duplexes to form combined ligated adaptor-target-adaptor sequences; wherein said adaptor polynucleotide construct contains at least one overhanging base that is modified such that the nucleic acid strand is resistant to exonucleolysis;
(c) preparing an amplification reaction comprising said combined ligated adaptor-target-adaptor sequences and at least two different primer oligonucleotides wherein said primer oligonucleotides are complementary to both a part of the adaptor polynucleotide sequence portion of the combined ligated adaptor-target-adaptor sequences, and complementary to at least one base of either the target polynucleotide duplexes, or an overhang attached to the target duplex;
(d) carrying out an amplification reaction in which said at least two different primer oligonucleotides are annealed to complementary parts of the adaptor-target-adaptor sequence and extended by sequential addition of nucleotides to generate amplification products complementary to at least one strand of the combined ligated adaptor-target-adaptor sequences and wherein said amplification products have common sequences at their 5' ends and common sequences at their 3' ends and collectively provide a library of template polynucleotide molecules.

A fourth aspect of the invention relates to the use of a library of template polynucleotide molecules prepared according to the method of the first, second or third aspects of the invention as a template for solid-phase nucleic acid amplification. Thus, in a particular embodiment the invention provides a method of solid-phase nucleic acid amplification of template polynucleotide molecules which comprises: preparing a library of template polynucleotide molecules which have common sequences at their 5' and 3' ends using the method according to the first, second or third aspects of the invention and carrying out a solid-phase nucleic acid amplification reaction wherein said template polynucleotide molecules are amplified.

Accordingly, the fourth aspect of the invention relates to methods wherein a library of template polynucleotide molecules prepared according to the method of the first, second or third aspects of the invention is used as a template for solid-phase nucleic acid amplification.

In a fifth aspect, the invention provides a kit for use in preparing a library of template polynucleotide molecules which have common sequences at their 5' and 3' ends wherein the common sequence at the 5' end of each individual template in the library is not identical and not fully complementary to the common sequence at the 3' end of said template, the kit comprising mismatched adaptor polynucleotides as defined herein in relation to the first, second or third aspects of the invention and oligonucleotide amplification primers capable of annealing to the mismatched adaptor polynucleotides.

DETAILED DESCRIPTION OF THE INVENTION

Figure 1:
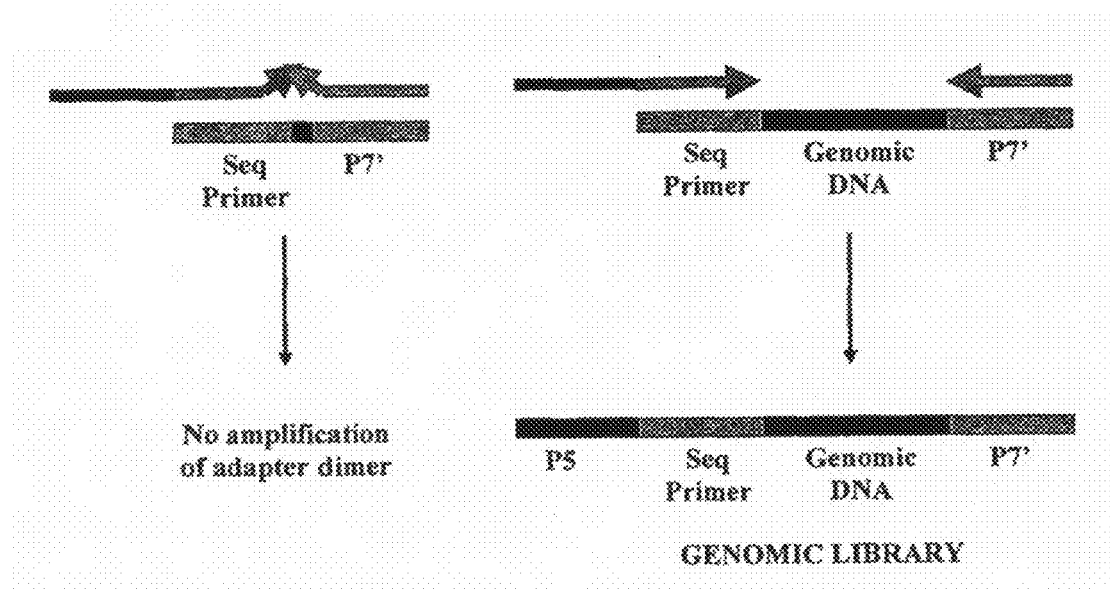
FIG. 1 shows a schematic of a modified PCR step whereby adaptor dimer amplification is reduced and an increased length of primers used in PCR.

The invention relates to a method of preparing a library of template polynucleotides which reduces and/or prevents the formation of adaptor-dimers during preparation of the library. As a result, the method of the invention is advantageous because it reduces the number of adaptor sequences recorded during any subsequent sequencing process.

As explained in further detail below, all templates within the library will contain regions of common sequence at (or proximal to) their 5' and 3' ends, wherein the common sequence at the 5' end of each individual template in the library is not identical and not fully complementary to the common sequence at the 3' end of said template.

The term 'library' refers to a collection or plurality of template molecules which share common sequences at their 5' ends and common sequences at their 3' ends. Use of the term 'library' to refer to a collection or plurality of template molecules should not be taken to imply that the templates making up the library are derived from a particular source, or that the 'library' has a particular composition. By way of example, use of the term 'library' should not be taken to imply that the individual templates within the library must be of different nucleotide sequence or that the templates be related in terms of sequence and/or source.

In its various embodiments, the invention encompasses formation of so-called 'monotemplate' libraries, which comprise multiple copies of a single type of template molecule, each having common sequences at their 5' ends and their 3' ends, as well as 'complex' libraries wherein many of the individual template molecules comprise different target sequences, although all share common sequences at their 5' ends and 3' ends. Such complex template libraries may be prepared using the method of the invention starting from a complex mixture of target polynucleotides such as (but not limited to) random genomic DNA fragments, cDNA libraries etc. The invention also extends to 'complex' libraries formed by mixing together several individual 'monotemplate' libraries, each of which has been prepared separately using the method of the invention starting from a single type of target molecule (i.e. a monotemplate), or libraries made from different 'complex' libraries further pooled. All templates in a given library will share common sequence at their 5' ends and common sequence at their 3' ends.

Use of the term 'template' to refer to individual polynucleotide molecules in the library merely indicates that one or both strands of the polynucleotides in the library are capable of acting as templates for template-dependent nucleic acid polymerisation catalysed by a polymerase. Use of this term should not be taken as limiting the scope of the invention to libraries of polynucleotides which are actually used as templates in a subsequent enzyme-catalysed polymerisation reaction.

The library of the invention is formed by first ligating identical adaptor polynucleotide molecules ('mismatched adaptors', the general features of which are defined below) to the 5' and 3' ends of one or more target polynucleotide duplexes (which may be of known, partially known or unknown sequence) to form adaptor-target constructs and then carrying out an initial primer extension reaction in which extension products complementary to both strands of each individual adaptor-target construct are formed. The resulting primer extension products, and optionally amplified copies thereof, collectively provide a library of template polynucleotides.

The adaptor polynucleotides used in the method of the invention are referred to herein as 'mismatched' adaptors because, as will be explained in detail herein, it is essential that the adaptors include a region of sequence mismatch, i.e. they must not be formed by annealing of fully complementary polynucleotide strands.

Mismatched adaptors for use in the invention are formed by annealing of two partially complementary polynucleotide strands so as to provide, when the two strands are annealed, at least one double-stranded region and at least one unmatched region.

The 'double-stranded region' of the adaptor is a short double-stranded region, typically comprising 5 or more consecutive base pairs, formed by annealing of the two partially complementary polynucleotide strands. This term simply refers to a double-stranded region of nucleic acid in which the two strands are annealed and does not imply any particular structural conformation.

Generally it is advantageous for the double-stranded region to be as short as possible without loss of function. By 'function' in this context is meant that the double-stranded region form a stable duplex under standard reaction conditions for an enzyme-catalysed nucleic acid ligation reaction, which will be well known to the skilled reader (e.g. incubation at a temperature in the range of from 4° C. to 25° C. in a ligation buffer appropriate for the enzyme), such that the two strands forming the adaptor remain partially annealed during ligation of the adaptor to a target molecule. It is not absolutely necessary for the double-stranded region to be stable under the conditions typically used in the annealing steps of primer extension or PCR reactions.

Since identical adaptors are ligated to both ends of each template molecule, the target sequence in each adaptor-target construct will be flanked by complementary sequences derived from the double-stranded region of the adaptors. The longer the double-stranded region, and hence the complementary sequences derived therefrom in the adaptor-target constructs, the greater the possibility that the adaptor-target construct is able to fold back and base-pair to itself in these regions of internal self-complementarity under the annealing conditions used in primer extension and/or PCR. Generally it is preferred for the double-stranded region to be 20 or less, 15 or less, or 10 or less base pairs in length in order to reduce this effect. The stability of the double-stranded region may be increased, and hence its length potentially reduced, by the inclusion of non-natural nucleotides which exhibit stronger base-pairing than standard Watson-Crick base pairs.

It is preferred, but not absolutely essential, for the two strands of the adaptor to be 100% complementary in the double-stranded region. It will be appreciated that one or more nucleotide mismatches may be tolerated within the double-stranded region, provided that the two strands are capable of forming a stable duplex under standard ligation conditions.

Adaptors for use in the invention will generally include a double-stranded region forming the 'ligatable' end of the adaptor, i.e. the end that is joined to a target polynucleotide in the ligation reaction. The ligatable end of the adaptor may be blunt or, in other embodiments, short 5' or 3' overhangs of one or more nucleotides may be present to facilitate/promote ligation. The 5' terminal nucleotide at the ligatable end of the adaptor should be phosphorylated to enable phosphodiester linkage to a 3' hydroxyl group on the target polynucleotide.

The term 'unmatched region' refers to a region of the adaptor wherein the sequences of the two polynucleotide strands forming the adaptor exhibit a degree of non-complementarity such that the two strands are not capable of fully annealing to each other under standard annealing conditions for a primer extension or PCR reaction. The unmatched region(s) may exhibit some degree of annealing under standard reaction conditions for a enzyme-catalysed ligation reaction, provided that the two strands revert to single stranded form under annealing conditions in an amplification reaction.

The adaptor constructs may contain exonuclease resistant modifications as described below. Such modifications lower the level of adaptor-dimers present in the library as the two adaptors can not undergo ligation without removal of their non complementary overhangs, which are non-complementary. The adaptors can be treated with an exonuclease enzyme, as described below, prior to the ligation reaction with the target, to ensure that the overhanging ends of the strands can not be removed during the ligation process. Treatment of the adaptors in this manner reduces the formation of the adaptor-dimers at the ligation step.

Each strand of each template molecule in the library formed in the primer extension reaction will therefore have the following structure, when viewed as a single strand:

5'-[common sequence I]-[target sequence]-[common sequence II]-3' wherein 'common sequence I' represents a sequence derived from copying a first strand of the mismatched adaptor and is common to all template molecules in the library generated in the initial primer extension reaction; 'target' represents a sequence derived from one strand of the target polynucleotide duplex and may be different in different individual template molecules within the library; and 'common sequence II' represents a sequence derived from copying of a second strand of the mismatched adaptor and is also common to all template molecules in the library generated in the initial primer extension reaction.

Since 'common sequence I' and 'common sequence II' are common to all template strands in the library they may include 'universal' primer-binding sequences, enabling all templates in the library to be ultimately amplified in a solid-phase PCR procedure using universal primers.

It is a key feature of the invention, however, that the common 5' and 3' end sequences denoted 'common sequence I' and 'common sequence II' are not fully complementary to each other, meaning that each individual template strand can contain different (and non-complementary) universal primer sequences at its 5' and 3' ends.

It is generally advantageous for complex libraries of templates to be amplified, for example by PCR or isothermal amplification (e.g. whole genome amplification), either in solution or on a solid support, to include regions of 'different' sequence at their 5' and 3' ends, which are nevertheless common to all template molecules in the library, especially if the amplification products are to be ultimately sequenced. For example, the presence of common unique sequence at one end only of each template in the library can provide a binding site for a sequencing primer, enabling one strand of each template in the amplified form of the library to be sequenced in a single sequencing reaction using a single type of sequencing primer. Equally the method of the invention may be applied to the preparation of libraries which are amplified in-vivo, such as for example bacterial cDNA libraries and the like.

Typically 'common sequence I' and 'common sequence II' will consist of no more than 100, or no more than 50, or no more than 40 consecutive nucleotides at the 5' and 3' ends, respectively, of each strand of each template polynucleotide. The precise length of the two sequences may or may not be identical. The nucleotide sequences of 'common sequence I' and 'common sequence II' in the template polynucleotides will be determined in part by the sequences of the adaptor strands ligated to the target polynucleotides and in part by the sequence of the primer used in the initial primer extension reaction, and any subsequent rounds of nucleic acid amplification.

In embodiments wherein the initial primer extension product is subjected to further amplification by conventional PCR, then the products of the amplification reaction will be double-stranded polynucleotides, one strand of which has the structure:
5'-[common sequence I]-[target sequence]-[common sequence II]-3'

It will be appreciated that 'common sequence II' in the amplification products may differ somewhat to the 'common sequence II' present in the products of the initial primer extension reaction, since the former will be determined in part by the sequence of the PCR primer used to prime synthesis of a polynucleotide strand complementary to the initial primer extension product, whereas the latter will be determined solely by copying of the adaptor sequences at the 3' ends of the adaptor-template constructs in the initial primer extension. Nevertheless, since the PCR primer is designed to anneal to a sequence in the initial extension products which is complementary to the 3' adaptor, the two forms of 'common sequence II' will contain identical sequence, at least at the 3' end. Additional sequence may be included at the 5' end of 'common sequence II' in the amplified products, for example by the use of 'tailed' PCR primers, as described in detail below. In other embodiments the common sequences present in the amplification products may actually be shorter than the common sequences included in the adaptors originally ligated to the target.

The precise nucleotide sequences of the common regions of the template molecules in the library are generally not material to the invention and may be selected by the user. The common sequences must at least comprise 'primer-binding' sequences which enable specific annealing of amplification primers when the templates are in use in a solid-phase amplification reaction. The primer-binding sequences are thus determined by the sequence of the primers to be ultimately used for solid-phase amplification. The sequence of these primers in turn is advantageously selected to avoid or minimise binding of the primers to the target portions of the templates within the library under the conditions of the amplification reaction, but is otherwise not particularly limited. By way of example, if the target portions of the templates are derived from human genomic DNA, then the sequences of the primers to be used in solid phase amplification should ideally be selected to minimise non-specific binding to any human genomic sequence.

The conditions encountered during the annealing steps of an amplification reaction will be generally known to one skilled in the art, although the precise annealing conditions will vary from reaction to reaction (see Sambrook et al., 2001, *Molecular Cloning, A Laboratory Manual*, 3rd Ed, Cold Spring Harbor Laboratory Press, Cold Spring Harbor Laboratory Press, NY; Current Protocols, eds Ausubel et al.). Typically such conditions may comprise, but are not limited to, (following a denaturing step at a temperature of about 94° C. for about one minute) exposure to a temperature in the range of from 40° C. to 72° C. (preferably 50-68° C.) for a period of about 1 minute in standard PCR reaction buffer.

Different annealing conditions may be used for a single primer extension reaction not forming part of a PCR reaction (again see Sambrook et al., 2001, *Molecular Cloning, A Laboratory Manual*, 3rd Ed, Cold Spring Harbor Laboratory Press, Cold Spring Harbor Laboratory Press, NY; Current Protocols, eds Ausubel et al.). Conditions for primer annealing in a single primer extension include, for example, exposure to a temperature in the range of from 30 to 37° C. in standard primer extension buffer. It will be appreciated that different enzymes, and hence different reaction buffers, may be used for a single primer extension reaction as opposed to a PCR reaction. There is no requirement to use a thermostable polymerase for a single primer extension reaction.

It is to be understood that the 'unmatched region' is provided by different portions of the same two polynucleotide strands which form the double-stranded region(s). Mismatches in the adaptor construct can take the form of one strand being longer than the other, such that there is a single stranded region on one of the strands, or a sequence selected such that the two strands do not hybridise, and thus form a single stranded region on both strands. The mismatches may also take the form of 'bubbles', wherein both ends of the adaptor construct(s) are capable of hybridising to each other and forming a duplex, but the central region is not. The portion of the strand(s) forming the unmatched region are not annealed under conditions in which other portions of the same two strands are annealed to form one or more double-stranded regions. For avoidance of doubt it is to be understood that a single-stranded or single base overhang at the 3' end of a polynucleotide duplex that subsequently undergoes ligation to the target sequences does not constitute an 'unmatched region' in the context of this invention.

The lower limit on the length of the unmatched region will typically be determined by function, for example the need to provide a suitable sequence for binding of a primer for primer extension, PCR and/or sequencing. Theoretically there is no upper limit on the length of the unmatched region, except that in general it is advantageous to minimise the overall length of the adaptor, for example in order to facilitate separation of unbound adaptors from adaptor-target constructs following the ligation step. Therefore, it is preferred that the unmatched region should be less than 50, or less than 40, or less than 30, or less than 25 consecutive nucleotides in length.

The precise nucleotide sequence of the adaptors is generally not material to the invention and may be selected by the user such that the desired sequence elements are ultimately included in the common sequences of the library of templates derived from the adaptors, for example to provide binding sites for particular sets of universal amplification primers and/or sequencing primers. Additional sequence elements may be included, for example to provide binding sites for sequencing primers which will ultimately be used in sequencing of template molecules in the library, or products derived from amplification of the template library, for example on a solid support. The adaptors may further include 'tag' sequences, which can be used to tag or mark template molecules derived from a particular source. The general features and use of such tag sequences is described in the applicant's pending application published as WO 05/068656.

Although the precise nucleotide sequence of the adaptor is generally non-limiting to the invention, the sequences of the individual strands in the unmatched region should be such that neither individual strand exhibits any internal self-complementarity which could lead to self-annealing, formation of hairpin structures etc. under standard annealing conditions. Self-annealing of a strand in the unmatched region is to be avoided as it may prevent or reduce specific binding of an amplification primer to this strand.

The mismatched adaptors are preferably formed from two strands of DNA, but may include mixtures of natural and non-natural nucleotides (e.g. one or more ribonucleotides) linked by a mixture of phosphodiester and non-phosphodiester backbone linkages. Other non-nucleotide modifications may be included such as, for example, biotin moieties, blocking groups and capture moieties for attachment to a solid surface, as discussed in further detail below.

The method comprises a first step of fragmenting one or more primary polynucleotide molecules to produce target polynucleotide duplexes.

As used herein, the term 'polynucleotide' refers to deoxyribonucleic acid (DNA), but where appropriate the skilled artisan will recognise that the method may also be applied to ribonucleic acid (RNA). The terms should be understood to include, as equivalents, analogs of either DNA or RNA made from nucleotide analogs and to be applicable to single stranded (such as sense or antisense) and double stranded polynucleotides. The term as used herein also encompasses cDNA, that is complementary or copy DNA produced from an RNA template, for example by the action of reverse transcriptase.

The primary polynucleotide molecules may originate in double-stranded DNA (dsDNA) form (e.g. genomic DNA fragments, PCR and amplification products and the like) or may have originated in single-stranded form, as DNA or RNA, and been converted to dsDNA form. By way of example, mRNA molecules may be copied into double-stranded cDNAs suitable for use in the method of the invention using standard techniques well known in the art. The precise sequence of the primary polynucleotide molecules is generally not material to the invention, and may be known or unknown.

In a particular embodiment, the primary polynucleotide molecules are DNA molecules. More particularly, the primary polynucleotide molecules represent the entire genetic complement of an organism, and are genomic DNA molecules which include both intron and exon sequence (coding sequence), as well as non-coding regulatory sequences such as promoter and enhancer sequences. Although it could be envisaged that particular sub-sets of polynucleotide sequences or genomic DNA could also be used, such as particular chromosomes, for example. Yet more particularly, the sequence of the primary polynucleotide molecules is not known. Still yet more particularly, the primary polynucleotide molecules are human genomic DNA molecules. The DNA target molecules may be treated chemically or enzymatically either prior to, or subsequent to any random fragmentation processes, and prior to or subsequent to the ligation of the adaptor sequences.

The sequence of the primary polynucleotide molecules may be the same or different, for example, a mixture of primary polynucleotide molecules of different sequences may be prepared by mixing a plurality of individual primary polynucleotide molecules. For example, DNA from more than one source can be prepared if each DNA sample is first tagged to enable its identification after it has been sequenced. Many different suitable DNA-tag methodologies already exist in the art and are well within the purview of the skilled person.

Random fragmentation refers to the fragmentation of a polynucleotide molecule in a non-ordered fashion by enzymatic, chemical or mechanical means. Such fragmentation methods are known in the art and utilise standard methods (Sambrook and Russell, Molecular Cloning, A Laboratory Manual, third edition). For the sake of clarity, generating smaller fragments of a larger piece of nucleic acid via specific PCR amplification of such smaller fragments is not equivalent to fragmenting the larger piece of nucleic acid because the larger piece of nucleic acid sequence remains in intact (i.e., is not fragmented by the PCR amplification). The random fragmentation is designed to produce fragments irrespective of the sequence identity or position of nucleotides comprising and/or surrounding the break. More particularly the random fragmentation is by mechanical means such as nebulisation or sonication to produce fragments of about 50 base pairs in length to about 1500 base pairs in length, still more particularly 50 to 700 base pairs in length, yet more particularly 50-400 base pairs in length. Most particularly, the method is used to generate smaller fragments of from 50-150 base pairs in length.

Fragmentation of polynucleotide molecules by mechanical means (nebulization, sonication and Hydroshear for example) results in fragments with a heterogeneous mix of blunt and 3'- and 5'-overhanging ends. It is therefore desirable to repair the fragment ends using methods or kits (such as the Lucigen DNA terminator End Repair Kit) known in the art to generate ends that are optimal for insertion, for example, into blunt sites of cloning vectors. In a particular embodiment, the fragment ends of the population of nucleic acids are blunt ended. More particularly, the fragment ends are blunt ended and phosphorylated. The phosphate moiety can be introduced during an enzymatic treatment, for example using polynucleotide kinase.

In a particular embodiment, the target polynucleotide sequences are prepared with single overhanging nucleotides by, for example, activity of certain types of DNA polymerase such as Taq polymerase or Klenow exo minus polymerase which has a nontemplate-dependent terminal transferase activity that adds a single deoxynucleotide, for example deoxyadenosine (A) to the 3' ends of, for example, PCR products. Such enzymes can be utilised to add a single nucleotide 'A' to the blunt ended 3' terminus of each strand of the target polynucleotide duplexes. Thus, an 'A' could be added to the 3' terminus of each end repaired duplex strand of the target polynucleotide duplex by reaction with Taq or Klenow exo minus polymerase whilst the adaptor polynucleotide construct could be a T-construct with a compatible 'T' overhang present on the 3' terminus of each duplex region of the adaptor construct. This end modification prevents self-ligation of both vector and target such that there is a bias towards formation of the combined ligated adaptor-target sequences.

The term 'target polynucleotide duplexes' refers to nucleic acid molecules that it is desired to sequence. The term 'template' refers to the target sequences ligated to the adaptor sequences; and thus the 'templates' are suitable for amplification; whereas the 'targets' without the adaptors are not.

The second step of the method comprises ligating a double stranded adaptor polynucleotide sequence to both ends of the target polynucleotide duplexes to form combined ligated adaptor-target-adaptor polynucleotide sequences. It is particularly advantageous to use the same adaptor construct for both ends of the target duplex, although two sets of adaptors can also be utilised.

Ligation methods are known in the art and utilise standard methods (Sambrook and Russell, Molecular Cloning, A Laboratory Manual, third edition). Such methods utilise ligase enzymes such as DNA ligase to effect or catalyse joining of the ends of the two polynucleotide strands of, in this case, the adaptor duplex construct and the target polynucleotide duplexes, such that covalent linkages are formed. The adaptor duplex construct may contain a 5'-phosphate moiety in order to facilitate ligation to the target 3'-OH. The target contains a 5'-phosphate moiety, either residual from the shearing process, or added using an enzymatic treatment step, and has been end repaired, and optionally extended by an overhanging base or bases, to give a 3'-OH suitable for ligation. In this context, joining means covalent linkage of polynucleotide strands which were not previously covalently linked. In a particular aspect of the invention, such joining takes place by formation of a phosphodiester linkage between the two polynucleotide strands, but other means of covalent linkage (e.g. non-phosphodiester backbone linkages) may be used:

Whilst the method of TA ligation (or TA cloning) is known in the art, the presence of the 'T' overhang does not fully remove the formation and presence of adaptor-dimer constructs in the library. The Inventors have made the surprising discovery that during ligation, even with an enzyme which is purported not to have measurable exonuclease activity, the overhanging nucleotide(s) is/are removed from the adaptors with surprising frequency. Thus even with the TA method of cloning, adaptor-dimers are not prevented. The deficiencies of the TA ligation protocol are addressed by the methods disclosed herein.

According to a particular aspect of the invention, in addition to the mismatched region previously described, the adaptor construct or constructs contains an overhanging base or bases at the 3'-end of one of the strands that is complementary to the overhanging base or bases at the 3'-end of the target duplexes, and a 5'-phosphate moiety on the complementary hybridised strand, The adaptor constructs may also contain a region on one, or both, of the strands that does not hybridise with a sequence on the other strand of the adaptor. Such 'mismatched' adaptors can serve as priming sites for further amplification reactions, and may allow for amplification with primers extending beyond the sequence of the ligated adaptor. Thus the region of known sequence in the template for amplification may be longer than the adaptor sequence ligated to the target. See FIG. 1.

The library of template polynucleotide molecules is particularly suitable for use in solid phase sequencing methods. Because sequence reads may be short, that is around 25-50 base pairs in length, unlike conventional methods of library preparation, it is of no consequence if multiple different target polynucleotide duplexes are ligated into a single template polynucleotide. Because the sequence read is shorter than the length of the individual target polynucleotide duplexes, there is no risk of artificial concatamers of sequence data being produced. The formation of target concatamers is minimised by the presence of an excess of the adaptor constructs.

Optionally the combined ligated polynucleotide sequences and unligated adaptor polynucleotide constructs may be purified from any components of the ligation reaction, such as enzymes, buffers, salts and the like. Suitable purification methods are known in the art and utilise standard methods (Sambrook and Russell, Molecular Cloning, A Laboratory Manual, third edition).

In a next step according to the invention an amplification reaction is prepared. The contents of an amplification reaction are known by one skilled in the art and include appropriate substrates (such as dNTPs), enzymes (e.g. a DNA polymerase) and buffer components required for an amplification reaction. Generally amplification reactions require at least two amplification primers, often denoted 'forward' and 'reverse' primers (primer oligonucleotides) that are capable of annealing specifically to a part of the polynucleotide sequence to be amplified under conditions encountered in the primer annealing step of each cycle of an amplification reaction. In certain embodiments the forward and reverse primers may be identical. Thus the primer oligonucleotides must include an 'adaptor-target specific portion', being a sequence of nucleotides capable of annealing to a part of, that is, a primer-binding sequence, in the polynucleotide molecule to be amplified (or the complement thereof if the template is viewed as a single strand) during the annealing step.

In the context of the present invention, the term 'polynucleotide molecule to be amplified' refers to the original or starting adaptor-target-adaptor sequence added to the amplification reaction. The 'adaptor-target specific portion' in the forward and reverse amplification primers refers to a sequence capable of annealing to the original or initial adaptor-target-adaptor present at the start of the amplification reaction and reference to the length of the 'adaptor-target specific portion' relates to the length of the sequence in the primer which anneals to the starting adaptor-target. It will be appreciated that if the primers contain any nucleotide sequence which does not anneal to the starting adaptor-target in the first amplification cycle then this sequence may be copied into the amplification products (assuming the primer does not contain a moiety which prevents read-through of the polymerase). Hence the amplified template strands produced in the first and subsequent cycles of amplification may be longer than the starting adaptor-target strands. Typically the invention relates to the use of forward and reverse primers of sufficient length to hybridise to the whole of the adaptor sequence and at least one base of the target sequence. The forward and reverse primers may also contain a region that extends beyond the adaptor construct, and therefore the amplification primers may be at least 20-100 bases in length. The forward and reverse primers may be of significantly different lengths; for example one may be 20-40 bases, and one may be 40-100 bases in length. The nucleotide sequences of the adaptor-target specific portions of the forward and reverse primers are selected to achieve specific hybridisation to the adaptor-target sequences to be amplified under the conditions of the annealing steps of the amplification reaction, whilst minimising non-specific hybridisation to any other target sequences present. Skilled readers will appreciate that it is not strictly required for the adaptor-target specific portion to be 100% complementary, a satisfactory level of specific annealing can be achieved with less than perfectly complementary sequences. In particular, one or two mismatches in the adaptor-target specific portion can usually be tolerated without adversely affecting specificity for the template. Therefore the term 'adaptor-target specific portion' should not be interpreted as requiring 100% complementarity with the adaptor-target. However, the requirement that the primers do not anneal non-specifically to regions of the adaptor-target other than their respective primer-binding sequences must be fulfilled.

Amplification primers are generally single stranded polynucleotide structures. They may also contain a mixture of natural and non-natural bases and also natural and non-natural backbone linkages, provided that any non-natural modifications do not preclude function as a primer—that being defined as the ability to anneal to a template polynucleotide strand during conditions of the amplification reaction and to act as an initiation point for synthesis of a new polynucleotide strand complementary to the template strand.

Primers may additionally comprise non-nucleotide chemical modifications, again provided such that modifications do not prevent primer function. Modifications may, for example, facilitate attachment of the primer to a solid support, for example a biotin moiety. Certain modifications may themselves improve the function of the molecule as a primer, or may provide some other useful functionality, such as providing a site for cleavage to enable the primer (or an extended polynucleotide strand derived therefrom) to be cleaved from a solid support.

To reduce the amplification of ligated adaptor-dimers, the Inventors have made the discovery that the forward and reverse amplification primers should anneal to at least one base 'originating' from the target nucleic acid fragment (described below). See FIG. 1. Such a base, or bases, can be part of the sequence of the target nucleic acid fragment, such as for example genomic sequence, or may be attached by a nucleotide tailing reaction, or by a ligation reaction and a subsequent cleavage reaction, for example with a restriction endonuclease. Attachment of a single nucleotide 3'-overhang is preferred. Accordingly the forward and reverse primers therefore contain the complementary base to the nucleotide triphosphate used in the target tailing reaction. The use of dATP in the enzymatic tailing reaction of the target nucleic acids means that the primers should contain a single overhang. This base can be chemically introduced during primer synthesis, or introduced enzymatically in a similar tailing reaction used to tail the blunt ended target nucleic acids. For the avoidance of doubt, any bases added to the target in treatment steps carried out before the adaptor ligation step are considered to originate from the attached target during the adaptor attachment process.

In order to accurately copy the target DNA sequence, it is desirable to use a DNA polymerase with a high fidelity. Such high fidelity polymerases often have a 'proofreading' exonuclease domain to read and remove incorrectly incorporated nucleotides. Such high fidelity polymerases include Phusion™ DNA polymerase, PfuUltra™ DNA polymerase, Deep Vent® DNA polymerase or KOD DNA polymerase The invention is directed to methods of using forward and reverse amplification primers, as described herein, designed such that the 3'-terminal base of the primers only hybridises to constructs that contain the target nucleic acid sequence, and not to adaptor dimers. This reduces amplification of the adaptor dimers, which is desirable to lower the number of adaptor-dimers from the template library. Not wishing to be bound by hypothesis, it is believed that since the primers have an additional 3' terminal base which only hybridises to the target nucleic acid sequence, and because such a base is not present in the adaptor-dimers, the 3' end of the primer forms a mis-matched end when hybridised to an adaptor-primer. The efficiency of the polymerase to extend this mis-matched end during amplification appears to be reduced. Hence the efficiency of amplification of adaptor-dimers is also reduced and the number of adaptor-primers contaminating a library is similarly lowered.

The Inventors have also made the further discovery that exonuclease activity of some polymerase enzymes used in an amplification reaction may, however, remove the terminal non hybridised bases from the amplification primers. This has the effect that amplification of the adaptor-dimers can occur, albeit at a reduced level. Therefore in a further particular embodiment of the invention, the amplification primers are modified to prevent removal of nucleotides from the 3'-end.

In a particular embodiment, the modification is a chemical modification. Exonucleoytic attack on the primer molecules can be efficiently prevented by the introduction of a single phosphorothioate bond at their 3'-termini (Nucleic Acids Research, 1992, 29, (14), 3551-4). Other such exonuclease resistant modifications may include phosphorodithioates, methyl phosphonates and 2'-O-methyl sugars, either separately or in combination. A number of other modifications are known to reduce the exonuclease degradation of single DNA strands, including phosphoramidites (P-NR2), phosphorofluoridates (P-F), boranophosphanes (P-BH3) or phosphoroselenoates (P-Se), and modifications to the sugar rings, such as 2'-O alkyl groups, 2'-fluoro groups, 2'-amino groups such as 2-amino propyl (PNAS, 1999, 96 (25) p 14240-45) or locked nucleic acids (LNA) where the 2' and 4' sugar positions are connected.

The amplification primers or adaptor constructs can optionally be treated with an exonuclease enzyme, for example a DNA polymerase with exonuclease activity, or exonuclease I, prior to use in the amplification reaction. In the case of the phosphorothioate modifications this removes the synthetic failure phosphate sequences, and also the phosphorothioate isomer that remains susceptible to exonucleolysis. The remaining material can be re-purified, if desired, then used in the amplification reaction. Such material is thereby completely resistant to exonucleolysis in the amplification reaction. Therefore the ability of the ligated adaptor-dimers to amplify is significantly reduced or even prevented, and they are thus removed from the library of ligated material. The result is that the efficiency of both amplification and/or sequencing of a library prepared according to the methods of the invention is significantly improved. This results in both a reduction of the costs of sequencing whilst increasing the quantity of useful sequence data.

The combination of both processes, namely the exonuclease treatment of the adaptor construct prior to ligation, to prevent the formation of the adaptor-dimers, and the exonuclease treatment of the amplification primers that overlap the target, to prevent amplification of the adaptor dimers is especially preferred, although both methods in isolation are within the scope of this invention.

Use of the Template Library

Template libraries prepared using any of the methods of the invention may be used in essentially any method of nucleic acid analysis which requires further amplification of the templates and/or sequencing of the templates or amplification products thereof. Exemplary uses of the template libraries include, but are not limited to, providing templates for whole genome amplification and also solid-phase PCR amplification or solid-phase isothermal amplification (of either monotemplate or complex template libraries). A particularly preferred use is in whole-genome amplification carried out on a solid-support.

Whole-Genome Amplification

Template libraries prepared according to the methods of the invention starting from a complex mixture of genomic DNA fragments representing a whole or substantially whole genome provide suitable templates for so-called 'whole-genome' amplification. The term 'whole-genome amplification' refers to a nucleic acid amplification reaction (e.g. PCR) in which the template to be amplified comprises a complex mixture of nucleic acid fragments representative of a whole (or substantially whole) genome.

Solid-Phase Amplification

Once formed, the library of templates prepared according to the methods described above can be used for solid-phase nucleic acid amplification.

Thus, in further aspects the inventions provide use of the methods in solid-phase nucleic acid amplification of template polynucleotide molecules which comprises: preparing a library of template polynucleotide molecules which have common sequences at their 5' and 3' ends using a method according to the first, second or third aspects of the invention described herein and carrying out a solid-phase nucleic acid amplification reaction wherein said template polynucleotide molecules are amplified.

The term 'solid-phase amplification' as used herein refers to any nucleic acid amplification reaction carried out on or in association with a solid support such that all or a portion of the amplified products are immobilised on the solid support as they are formed. In particular, the term encompasses solid-phase polymerase chain reaction (solid-phase PCR) and solid phase isothermal amplification which are reactions analogous to standard solution phase amplification, except that one or both of the forward and reverse amplification primers is/are immobilised on the solid support. Solid phase PCR covers systems such as emulsions, wherein one primer is anchored to a bead and the other is in free solution, and colony formation in solid phase gel matrices wherein one primer is anchored to the surface, and one is in free solution.

Although the invention encompasses 'solid-phase' amplification methods in which only one amplification primer is immobilised (the other primer usually being present in free solution), it is preferred for the solid support to be provided with both the forward and the reverse primers immobilised. In practice, there will be a 'plurality' of identical forward primers and/or a 'plurality' of identical reverse primers immobilised on the solid support, since the amplification process requires an excess of primers to sustain amplification. References herein to forward and reverse primers are to be interpreted accordingly as encompassing a 'plurality' of such primers unless the context indicates otherwise.

As will be appreciated by the skilled reader, any given amplification reaction requires at least one type of forward primer and at least one type of reverse primer specific for the template to be amplified. However, in certain embodiments the forward and reverse primers may comprise template-specific portions of identical sequence, and may have entirely identical nucleotide sequence and structure (including any non-nucleotide modifications). In other words, it is possible to carry out solid-phase amplification using only one type of primer, and such single-primer methods are encompassed within the scope of the invention. Other embodiments may use forward and reverse primers which contain identical template-specific sequences but which differ in some other structural features. For example one type of primer may contain a non-nucleotide modification which is not present in the other.

In other embodiments of the invention the forward and reverse primers may contain template-specific portions of different sequence.

In all embodiments of the invention, primers for solid-phase amplification are preferably immobilised by covalent attachment to the solid support at or near the 5' end of the primer, leaving the template-specific portion of the primer free to anneal to its cognate template and the 3' hydroxyl group free for primer extension. Any suitable covalent attachment means known in the art may be used for this purpose. The chosen attachment chemistry will depend on the nature of the solid support, and any derivatisation or functionalisation applied to it. The primer itself may include a moiety, which may be a non-nucleotide chemical modification, to facilitate attachment. In one particularly preferred embodiment the primer may include a sulphur-containing nucleophile, such as phosphorothioate or thiophosphate, at the 5' end. In the case of solid-supported polyacrylamide hydrogels (as described below), this nucleophile will bind to a bromoacetamide group present in the hydrogel. A more particular means of attaching primers and templates to a solid support is via 5' phosphorothioate attachment to a hydrogel comprised of polymerised acrylamide and N-(5-bromoacetamidylpentyl) acrylamide (BRAPA).

The library may be amplified on beads wherein each bead contains a forward and reverse amplification primer. It is preferred to use the library of templates prepared according to the first, second or third aspects of the invention to prepare clustered arrays of nucleic acid colonies, analogous to those described in WO 00/18957 and WO 98/44151, by solid-phase amplification and more particularly solid phase isothermal amplification. The terms 'cluster' and 'colony' are used interchangeably herein to refer to a discrete site on a solid support comprised of a plurality of identical immobilised nucleic acid strands and a plurality of identical immobilised complementary nucleic acid strands. The term 'clustered array' refers to an array formed from such clusters or colonies. In this context the term 'array' is not to be understood as requiring an ordered arrangement of clusters.

The term solid phase, or surface, is used to mean either a planar array wherein primers are attached to a flat surface, for example glass, silica or plastic microscope slides or similar flow cell devices; beads, wherein either one or two primers are attached to the beads and the beads are amplified; or an array of beads on a surface after the beads have been amplified.

Clustered arrays can be prepared using either a process of thermocycling, as described in patent WO9844151, or a process whereby the temperature is maintained as a constant, and the cycles of extension and denaturing are performed using changes of reagents. Such isothermal amplification methods are described in patent application number US60/783,618 (Isothermal methods for creating clonal single molecule arrays). Due to the lower temperatures required in the isothermal process, this is particularly preferred.

Use in Sequencing/Methods of Sequencing

The invention also encompasses methods of sequencing amplified nucleic acids generated by whole genome or solid-phase amplification. Thus, the invention provides a method of nucleic acid sequencing comprising amplifying a library of nucleic acid templates using whole genome or solid-phase amplification as described above and carrying out a nucleic acid sequencing reaction to determine the sequence of the whole or a part of at least one amplified nucleic acid strand produced in the whole genome or solid-phase amplification reaction.

Sequencing can be carried out using any suitable sequencing technique, wherein nucleotides are added successively to a free 3' hydroxyl group, resulting in synthesis of a polynucleotide chain in the 5' to 3' direction. The nature of the nucleotide added is preferably determined after each nucleotide addition. Sequencing techniques using sequencing by ligation, wherein not every contiguous base is sequenced, and techniques such as massively parallel signature sequencing (MPSS) where bases are removed from, rather than added to the strands on the surface are also within the scope of the invention, as are techniques using detection of pyrophosphate release (pyrosequencing). Such pyrosequencing based techniques are particularly applicable to sequencing arrays of beads where the beads have been amplified in an emulsion such that a single template from the library molecule is amplified on each bead.

The initiation point for the sequencing reaction may be provided by annealing of a sequencing primer to a product of the whole genome or solid-phase amplification reaction. In this connection, one or both of the adaptors added during formation of the template library may include a nucleotide sequence which permits annealing of a sequencing primer to amplified products derived by whole genome or solid-phase amplification of the template library.

The products of solid-phase amplification reactions wherein both forward and reverse amplification primers are covalently immobilised on the solid surface are so-called 'bridged' structures formed by annealing of pairs of immobilised polynucleotide strands and immobilised complementary strands, both strands being attached to the solid support at the 5' end. Arrays comprised of such bridged structures provide inefficient templates for nucleic acid sequencing, since hybridisation of a conventional sequencing primer to one of the immobilised strands is not favoured compared to annealing of this strand to its immobilised complementary strand under standard conditions for hybridisation.

In order to provide more suitable templates for nucleic acid sequencing it is preferred to remove substantially all or at least a portion of one of the immobilised strands in the 'bridged' structure in order to generate a template which is at least partially single-stranded. The portion of the template which is single-stranded will thus be available for hybridisation to a sequencing primer. The Process of removing all or a portion of one immobilised strand in a 'bridged' double-stranded nucleic acid structure may be referred to herein as 'linearisation'.

Bridged template structures may be linearised by cleavage of one or both strands with a restriction endonuclease or by cleavage of one strand with a nicking endonuclease. Other methods of cleavage can be used as an alternative to restriction enzymes or nicking enzymes, including inter alia chemical cleavage (e.g. cleavage of a diol linkage with periodate), cleavage of abasic sites by cleavage with endonuclease (for example 'USER', as supplied by NEB, part number M5505S), or by exposure to heat or alkali, cleavage of ribonucleotides incorporated into amplification products otherwise comprised of deoxyribonucleotides, photochemical cleavage or cleavage of a peptide linker.

It will be appreciated that a linearization step may not be essential if the solid-phase amplification reaction is performed with only one primer covalently immobilised and the other in free solution.

In order to generate a linearised template suitable for sequencing it is necessary to remove 'unequal' amounts of the complementary strands in the bridged structure formed by amplification so as to leave behind a linearised template for sequencing which is fully or partially single stranded. Most preferably one strand of the bridged structure is substantially or completely removed.

Following the cleavage step, regardless of the method used for cleavage, the product of the cleavage reaction may be subjected to denaturing conditions in order to remove the portion(s) of the cleaved strand(s) that are not attached to the solid support. Suitable denaturing conditions, for example sodium hydroxide solution, formamide solution or heat, will be apparent to the skilled reader with reference to standard molecular biology protocols (Sambrook et al., 2001, *Molecular Cloning, A Laboratory Manual,* 3rd Ed, Cold Spring Harbor Laboratory Press, Cold Spring Harbor Laboratory Press, NY; Current Protocols, eds Ausubel et al.).

Denaturation (and subsequent re-annealing of the cleaved strands) results in the production of a sequencing template which is partially or substantially single-stranded. A sequencing reaction may then be initiated by hybridisation of a sequencing primer to the single-stranded portion of the template.

Thus, the invention encompasses methods wherein the nucleic acid sequencing reaction comprises hybridising a sequencing primer to a single-stranded region of a linearised amplification product, sequentially incorporating one or more nucleotides into a polynucleotide strand complementary to the region of amplified template strand to be sequenced, identifying the base present in one or more of the incorporated nucleotide(s) and thereby determining the sequence of a region of the template strand.

One preferred sequencing method which can be used in accordance with the invention relies on the use of modified nucleotides having removable 3' blocks, for example as described in WO04018497. Once the modified nucleotide has been incorporated into the growing polynucleotide chain complementary to the region of the template being sequenced there is no free 3'-OH group available to direct further sequence extension and therefore the polymerase can not add further nucleotides. Once the nature of the base incorporated into the growing chain has been determined, the 3' block may be removed to allow addition of the next successive nucleotide. By ordering the products derived using these modified nucleotides it is possible to deduce the DNA sequence of the DNA template. Such reactions can be done in a single experiment if each of the modified nucleotides has a different label attached thereto, known to correspond to the particular base, to facilitate discrimination between the bases added during each incorporation step. Alternatively, a separate reaction may be carried out containing each of the modified nucleotides separately.

The modified nucleotides may carry a label to facilitate their detection. Preferably this is a fluorescent label. Each nucleotide type may carry a different fluorescent label, for example as described in U.S. Provisional Application No. 60/801,270 (Novel dyes and the use of their labelled conjugates). However the detectable label need not be a fluorescent label. Any label can be used which allows the detection of an incorporated nucleotide.

One method for detecting fluorescently labelled nucleotides comprises using laser light of a wavelength specific for the labelled nucleotides, or the use of other suitable sources of illumination. The fluorescence from the label on the nucleotide may be detected by a CCD camera or other suitable detection means. Suitable instrumentation for recording images of clustered arrays is described in U.S. Provisional Application No. 60/788,248 (Systems and devices for sequence by synthesis analysis).

The invention is not intended to be limited to use of the sequencing method outlined above, as essentially any sequencing methodology which relies on successive incorporation of nucleotides into a polynucleotide chain can be used. Suitable alternative techniques include, for example, Pyrosequencing™, FISSEQ (fluorescent in situ sequencing), MPSS and sequencing by ligation-based methods.

The target polynucleotide to be sequenced using the method of the invention may be any polynucleotide that it is desired to sequence. Using the template library preparation method described in detail herein it is possible to prepare template libraries starting from essentially any double or single-stranded target polynucleotide of known, unknown or partially known sequence. With the use of clustered arrays prepared by solid-phase amplification it is possible to sequence multiple targets of the same or different sequence in parallel.

Kits

The invention also relates to kits for use in preparing libraries of template polynucleotides using the method of the first, second or third aspects of the invention.

Preferred embodiments of the kit comprise at least a supply of a mismatched adaptor as defined herein, plus a supply of at least one amplification primer which is capable of annealing to the mismatched adaptor and at least one base originating from the attached target, and priming synthesis of an extension product, which extension product would include any target sequence ligated to the adaptor when the adaptor is in use.

The preferred features of the 'mismatch' adaptors for inclusion in the kit are as described elsewhere herein in relation to other aspects of the invention. The structure and properties of amplification primers will be well known to those skilled in the art. Suitable primers of appropriate nucleotide sequence for use with the adaptors included in the kit can be readily prepared using standard automated nucleic acid synthesis equipment and reagents in routine use in the art. The kit may include a supply of one single type of primer or separate supplies (or even a mixture) of two different primers, for example a pair of amplification primers suitable for PCR or isothermal amplification of templates modified with the mismatched adaptor in solution phase and/or on a suitable solid support (i.e. solid-phase amplification).

In one embodiment the kit may include supplies of different primer-pairs for use in solution phase and solid phase PCR and more particularly isothermal amplification. In this context the 'different' primer-pairs may be of substantially identical nucleotide sequence but differ with respect to some other feature or modification, such as for example surface-capture moieties, etc. In other embodiments the kit may include a supply of primers for use in an initial primer extension reaction and a different primer-pair (or pairs) for solution and/or solid phase amplification.

Adaptors and/or primers may be supplied in the kits ready for use, or more preferably as concentrates requiring dilution before use, or even in a lyophilised or dried form requiring reconstitution prior to use. If required, the kits may further include a supply of a suitable diluent for dilution or reconstitution of the primers. Optionally, the kits may further comprise supplies of reagents, buffers, enzymes, dNTPs, etc., for use in carrying out PCR or isothermal amplification. Suitable (but non-limiting) examples of such reagents are as described in the Materials and Methods sections of the accompanying Examples. Further components which may optionally be supplied in the kit include 'universal' sequencing primers suitable for sequencing templates prepared using the mismatched adaptors and primers.

The invention will be further understood with reference to the following non-limiting experimental example:

EXAMPLE 1

The DNA source used was a purified 10 kb region of Human BAC. The DNA was first prepared for ligation to forked adaptors by: fragmentation of the DNA by nebulisation, end repair of the DNA ends to make them blunt-ended and phosphorylation, then the addition of a single 'A' nucleotide onto the 3' ends of the DNA fragments. The ligation reaction was performed with the prepared fragmented DNA and adaptors pre-formed by annealing 'Oligo A' and 'Oligo B' (sequences given below). The product of the reaction was isolated/purified from unligated adaptor by gel electrophoresis. Finally, the product of the ligation reaction was subjected to cycles of PCR to selectively amplify ligated product that contained genomic DNA with adaptor at both ends of the fragments.

Materials and Methods

DNA Sample Preparation

Amplified 10 kb region of human BAC DNA (140K human chromosome 6 insert in a pTARBAC vector) using two 5' phosphorylated primers (LRPCR primer 1: 5'Phosphate TGGAACAGCCGCTCTCACCT SEQ ID NO:1 and LRPCR primer 2: 5'Phosphate TCCTGGAGGGAAGTGACTAT SEQ ID NO:2). Used 0.5 µM each primer, 200 µM each dNTP, 0.02 ng/µl BAC DNA, 0.02 U/µl Phusion™ polymerase (NEB/Finnzymes #F530S), diluted in 1× Finnzymes GC buffer.

PCR Programme:

| | |
|---|---|
| 98° C. 2 mins | |
| 98° C. 30 secs | |
| 60° C. 30 secs | } 35 cycles |
| 72° C. 5.5 mins | |
| 72° C. 10 mins | |
| Hold at 4° C. | |

Gel purified 10 kb product on 0.7% TAE agarose gel, using Qiagen gel extraction kit (Qiagen #28706), according to manufacturer's instructions.

Nebulization

Materials:
  10 kb region of human BAC (from above)
  Buffer (glycerol 53.1 ml, water 42.1 ml, 1 M TrisHCl (pH7.5) 3.7 ml, 0.5 M EDTA 1.1 ml)
  Nebulizer Invitrogen (#K7025-05)
  Qiagen columns PCR purification kit #28104

Mix: 100 µl (0.8 micrograms) of DNA
  660 µl Buffer

Procedure:

Chilled DNA solution was fragmented in the nebulizer on ice for 6 minutes under 32 pounds per square inch (psi) of pressure. The recovered volume was purified with a Qiagen PCR purification kit column and eluted in 30 µl of EB (Qiagen).

End-Repair

Materials:

| | |
|---|---|
| T4 DNA Polymerase | NEB #M0203L |
| 10xNEB 2 buffer | NEB #B7002S |
| 100x BSA | NEB #B9001S |
| dNTPs mix (10 mM each) | NEB #N0447S |
| E. coli DNA Pol I large fragment (Klenow) | NEB #M0210S |
| T4 polynucleotide kinase | NEB #M0201L |
| T4 PNK buffer | NEB #B0201S |
| 100 mM ATP | Amersham #27-2056-01 |
| Qiagen columns | PCR purification kit #28104 |

End repair mix was assembled as follows:

| | |
|---|---|
| DNA | 30 µl |
| Water | 7.5 µl |
| 10xNEB2 | 5 µl |
| 100xBSA | 0.5 µl |
| 10 mM dNTPs | 2 µl |
| T4 DNA pol (3 U/µl) | 5 µl |
| | 50 µl total |

The reaction was incubated for 15 min at room temperature, then 1 µl of E. coli DNA Pol I large fragment (Klenow) was added and the reaction incubated for a further 15 min at room temperature. The DNA was purified from enzymes, buffer, etc. by loading the reaction mix on a Qiagen column, and eluting in 30 µl EB (Qiagen). The 5' ends of the DNA were then phosphorylated using polynucleotide kinase as follows:

| | |
|---|---|
| DNA | 30 µl |
| Water | 9.5 µl |
| 10xPNK buffer | 5 µl |
| 100 mM ATP | 0.5 µl |
| T4 PNK (10 U/µl) | 5 µl |
| | 50 µl total |

The reaction was incubated for 30 min at 37° C., then heat inactivated at 65° C. for 20 min. DNA was then purified from enzymes, buffer, etc by loading the reaction mix on a Qiagen column, finally eluting in 30 µl EB (Qiagen).

A—Tailing Reaction

Materials:

| | |
|---|---|
| Taq DNA polymerase | NEB #M0267S |
| 10x thermopol buffer | NEB #B9004S |
| 1 mM dATP | Amersham-Pharmacia #272050 |
| Qiagen MinElute column | PCR purification kit #28004 |

The following reaction mix was assembled:

| | |
|---|---|
| DNA | 30 µl |
| 10x thermopol buffer | 5 µl |
| 1 mM dATP | 10 µl |
| Taq pol (5 U/µl) | 3 µl |
| | ~50 µl total |

The reaction was incubated for 30 min at 70° C., then the DNA purified from enzymes, buffer, etc. by loading the reaction mix on a Qiagen MinElute column, eluting in 10 µl EB (Qiagen).

Anneal Forked Adaptor

Materials:

```
Oligo A:
                                           SEQ ID NO: 3
5'ACACTCTTTCCCTACACGACGCTCTTCCGATCxT
(x = phosphorothioate bond)
```

```
Oligo B:
                                           SEQ ID NO: 4
5'Phosphate-GATCGGAAGAGCTCGTATGCCGTCTTCTGCTTG
```

50 mM Tris/50 mM NaCl pH7

PCR machine

| | |
|---|---|
| 100 µM Oligo A | 20 µl |
| 100 µm Oligo B | 20 µl |
| Tris/NaCl | 10 µl |
| | 50 µl at 40 µM duplex in 10 mM Tris/10 mM NaCl (pH 7.5) |

The adaptor strands were annealed in a PCR machine programmed as follows:

Ramp at 0.5° C./sec to 97.5° C.

Hold at 97.5° C. for 150 sec

Then a step of 97.5° C. for 2 sec with a temperature drop of 0.1° C./cycle for 775 cycles Forked adaptor was diluted to 15 µM final concentration in 10 mM Tris/10 mM NaCl (pH 7.5).

Ligation Reaction

Materials:

| | |
|---|---|
| 15 µM forked adaptor (from above) | |
| A-tailed genomic DNA (from above) | |
| Quick Ligase | NEB #M2200L |
| Quick Ligase 2x buffer | NEB #B2200S |
| PCR machine | |
| Qiagen columns | PCR purification kit #28104 |

Reaction mix was assembled as follows:

| | |
|---|---|
| DNA | 10 µl |
| 2x buffer | 25 µl |
| 15 µM adaptor | 10 µl |
| Quick Ligase | 5 µl |
| | 50 µl total |

The reaction was incubated for 30 min at room temperature, then the DNA purified from enzymes, buffer, etc. by loading the reaction mix on a Qiagen column, and eluting in 30 µl EB (Qiagen).

Gel Purification

Materials:

| | |
|---|---|
| Agarose | Biorad #161-3101 |
| 100 base pair ladder | NEB #N3231L |
| TAE | |
| Loading buffer (50 mM Tris pH8, 40 mM EDTA, 40% w/v sucrose) | |
| Ethidium bromide | |
| Gel trays and tank. Electrophoresis unit | |
| Qiagen MinElute columns | Qiagen(#28004) |

The entire sample from the purified ligation reaction was loaded into one lane of a 2% agarose gel containing ethidium bromide and run at 120V for 50 min. The gel was then viewed on a 'White-light' box and fragments from 300 bp to 700 bp excised and purified with two minElute columns, eluting each in 15 µl EB (Qiagen) and pooled.

PCR Amplification

Materials:

Gel purified ligated DNA (from above)

```
PCR PRIMER 1:
                                          SEQ ID NO: 5
5'AATGATACGGCGACCACCGAGATCTACACTCTTTCCCTACACGACGCT

CTTCCGATCyT,
where y = phosphorothioate bond and 2'-OMe

PCR PRIMER 2:
                                          SEQ ID NO: 6
5' CAAGCAGAAGACGGCATACGAGCTCTTCCGATCyT,
where y = phosphorothioate bond and 2'-OMe
```

| | |
|---|---|
| DeepVent | NEB #M0258L |
| 10x Thermopol buffer | NEB #B9004S |
| dNTPs mix (10 mM each) | NEB #N0447S |
| PCR machine | |
| Qiagen columns | PCR purification kit #28104 |

The PCR reaction was prepared as follows:

| | |
|---|---|
| DNA | 1 µl |
| 10x Thermopol buffer | 5 µl |
| dNTPs (10 mM each) | 1 µl |
| 25 µM PCR primer 1 | 1 µl |
| 25 µM PCR primer 2 | 1 µl |
| DeepVent | 1 µl |
| Water | 40 µl |
| | 50 µl total |

Thermocycling was carried out in a PCR machine under the following conditions:

2 min @ 94° C.

[45 sec@ 94° C., 45 sec @ 65° C., 2 min @ 70° C.] 18 cycles 5 min @ 70° C.

Hold @ 4° C.

PCR products were purified from enzymes, buffer, etc. on a Qiagen column, eluting in 30 µl EB (Qiagen). The resulting DNA library is ready for amplification on a surface amplification platform.

Validation of Library by Gel Analysis 3 ul of library was run on a 4-20% TBE PAGE gel (Invitrogen #EC62252) and stained in Vistra green stain according to manufacturer's instructions (Amersham, RPN5786). The stained DNA was visualised using a Typhoon scanner and is shown below. The library was amplified (visualised as a smear from 300-700 bp) and no adaptor dimer (forked adaptor that has ligated to itself) was visible by eye using PCR primers 1 and 2 (from above), which have a phosphorothioate bond and 2'-OMe modification. Using the other 2 sets of primers (unmodified and modified with 3' phosphorothioate), the genomic library was amplified, but so was the adaptor dimer. The phosphorothioate bond and 2'-OMe modification of the primers prevents adaptor dimer amplification with DeepVent polymerase.

Figure 2:
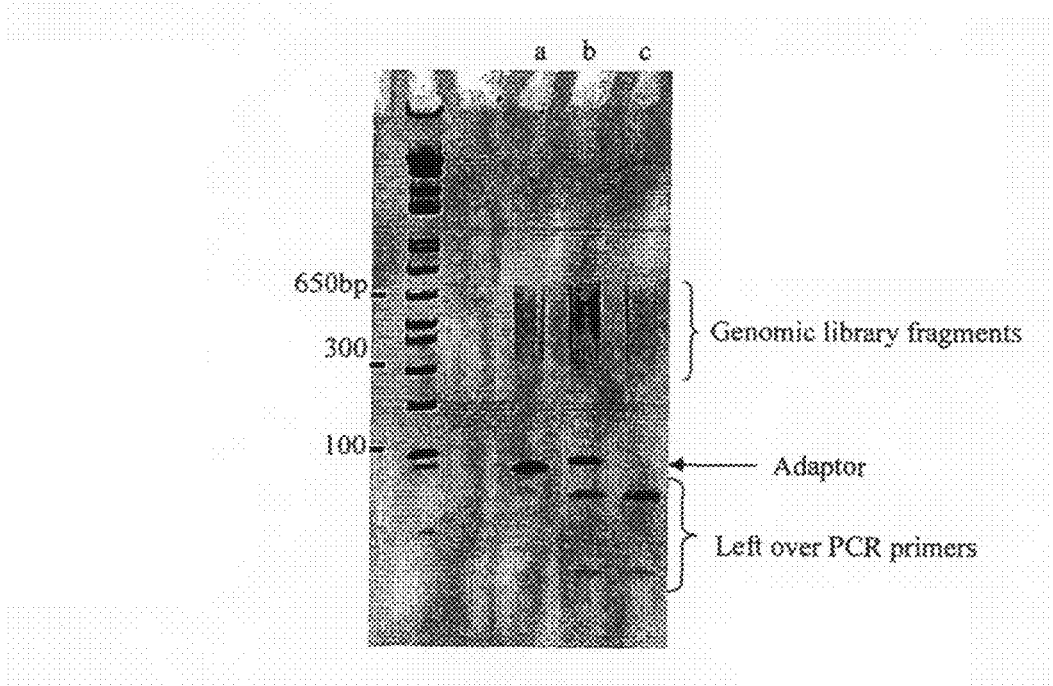
FIG. 2 shows a scan of a polyacrylamide gel stained to visualize DNA following electrophoresis. The lanes are as follows: M) marker lane; a) Amplification of library using unmodified PCR primers; b) Amplification of library using PCR primers having a phosphorothioate bond modification; c) Amplification of library using PCR primers having a phosphorothioate bond and 2'-OMe modification.

FIG. 2 shows a 4-20% TBE PAGE gel (Invitrogen, EC62252) of 3 µl of purified library, stained in Vistra green stain according to manufacturer's instructions (Amersham, RPN5786).

M) Marker lane a) Amplification of library using unmodified PCR primers (AATGATACGGCGACCACCGA-CACTCTTTCCCTACACGACGCTCTTCCGATCT SEQ ID NO:7 and CAAGCAGAAGACGGCATAC-GAGCTCTTCCGATCT SEQ ID NO:8).

b) Amplification of library using PCR primers, which have a phosphorothioate bond modification (AATGATACG-GCGACCACCGAGATCTACACTCTTTC-CCTACACGACGCTCTTCCG ATCxT SEQ ID NO:9 and CAAGCAGAAGACGGCATACGAGCTCTTC-CGATCxT SEQ ID NO:10, where x is a phosphorothioate bond).

c) Amplification of library using PCR primers, which have a phosphorothioate bond and 2'-OMe modification (see PCR amplification method above).

Validation of Library by Conventional Sanger Sequencing

4 µl of the library was cloned into a plasmid vector (Zero Blunt TOPO PCR cloning kit, Invitrogen #K2800-20) and plated out on agar, according to manufacturer's instructions. Colonies were picked, mini-prepped and the cloned inserts sequenced by conventional Sanger sequencing.

These results confirm that the library preparation method produces a library of 'sequenceable' DNA templates containing a mixture of genomic fragments of different sequence, flanked by the two adaptors (AATGATACGGCGACCAC-CGAGATCTACACTCTTTCCCTACAC-GACGCTCTTCCGATCT SEQ ID NO:7 and AGATCG-GAAGAGCTCGTATGCCGTCTTCTGCTTG SEQ ID NO:11), required for cluster formation and SBS sequencing. The insert DNA from each of the clones sequenced was found to align to the human BAC reference sequence. The genomic DNA is amplified with low error rates by using Deep Vent®, a high fidelity polymerase. The adaptor sequences have no mutations/deletions at adaptor-genomic DNA boundaries, which should allow the hybridisation of the SBS sequencing primer and successful SBS sequencing of inserts. None of the clones were adaptor dimers (lacked genomic insert).

Conventional Sanger Sequencing of 20 Clones from Library.

```
Clone 1
                                         SEQ ID NO: 16
CAAGCAGAAGACGGCATACGAGCTCTTCCGATCTGCTGGAGGGAAATCCA

AACTCAGGGGTGCCTGTGCCACAGCAAACACTCTCCCTCTCACACCACCT

GGAATAGAGATCAGCTAGAGCAGAGGCTGCTAAGAGAGGGAACAGAGGCT

CCTTGTGACAGGGAGACTAGGATCAGAAGTCAGGGAAGGGACAGCCGGGT

GAAATGACTGGAAAGAGGAGCAATCACTCAGCAGTAAGGCAGGTTCTTCC

AAAGACAAAAGGACACAGAGATAAGTCAGGGCACTTCCAAGGAACCCAAC

TACCTACTCCACACTCCCAAATTTATTCTGGGTTGGGCCCTTTTTGGTTC

CAATATCACCTCGGATACCATAACTTGTCCAAGGTCTCTTCTTACCTCTC

CCACCCTAAATGAAGACGGGCCCAGATCGGAAGAGCGTCGTGTAGGGAAA

GAGTGTAGATCTCGGTGGTCGCCGTATCATT

Clone 2
                                         SEQ ID NO: 17
ATTTAAATTTGGGGAACCATTGATGGATATAAGTGGTATTTAAAGCCACA

GGATTAGGCTGGGCACAGTGGCTCATGCCTATAATCCCAGCCCTTTGGGA

GGCTGAGGCAGGTGGATCACTTGAGGCCAGGAGTTTGAGACCAGCCTGGC

CAACATGGTGAAACCCTGTCTCTACCAAAAAATACAGAAAATTAGCCGTG
```

TGTGGTGGTGCGTGCCTGTAGTCCCAGATACTCAGGAGGGTGAGGCAGGA

GAATTGCTTGAATCAGATCGGAAGAGCTCGTATGCCGTCTTCTGCTTG

Clone 3

SEQ ID NO: 18

CAAGCAGAAGACGGCATACGAGCTCTTCCGATCTGGCCCCGCCAGCTCTT

GTGGTTGCCTGGAAGCATTATTTCCATCAACACTATCCCCAGCTCCACGT

CGTCCTTTTCACCTCTTTTCCTCGGGACCCCCGCACCCCACAGGATCCTA

GTAGTGGTGAGTGGGCAATGAGAGAGGGCAACTTGGGAGAGGTGAGTTGG

CAGGGGACAAAGGGGAGAACAGAGAGGCTTATTGACAAGGGGGCACCTGG

TCTTGGGCCTAAGGGTGGTGGGAGATCGGAAGAGCGTCGTGTAGGGAAAG

AGTGTAGATCTCGGTGGTCGCCGTATCATT

Clone 4

SEQ ID NO: 19

CAAGCAGAAGACGGCATACGAGCTCTTCCGATCTTTTGCCATTTCCACAG

CAGTATGTCCCATCCCTAGAATATCTGGCACCTGGTTAAGTGTTCAGTAC

ATATTTGTTGAATGGGTAAATGAATGAGAGCTGGAGGGAAATCCAAACTC

AGGGGTGCCTGTGCCACAGCAAACACTCTCCCTCTCACACCACCTGGAAT

AGAGATCAGCTAGAGCAGAGGCTGCTAAGAGAGGGAACAGAGGCTCCTTG

TGACAGGGAGACTAGGATCAGAAGATCGGAAGAGCGTCGTGTAGGAAAGA

GTGTAGATCTCGGTGGTCGCCGTATCATT

Clone 5

SEQ ID NO: 20

AATGATACGGCGACCACCGAGATCTACACTCTTTCCCTACACGACGCTCT

TCCGATCTGCACAATTTCAGTTCTATCAAGTTTGAAAGCTGCAAAATTAA

GCTGCATTGTTGAGAGATACACAGGTCATAAACTAAAGAGAAATGTAAGG

AGTTGATTTCCTTAAAAGGATAAAGCTTGCATGTATAGAGGGAGAGGATT

ATGATCAAGAAGGATGAGTGGCGGCCGGTATGGTGGCTCATCCCTGTAAT

CCTAGCACTTTGGGAGGCTGAGGCAGGCGCATTACTTGAGGTCAGGAGTT

TGAGACCAGCCTGGCCAACATGGCAAAACCCTATCTCTACTAAAAATACA

AAAAGTTAGCCAGGTGTGGAGCCGCACGCCTGTGGTCTCAGCTACTCAGG

AGGTTGAGGCACGAGAATCGCTTGAACCTGGGAGGATGAGGTTGTAGTGA

GCCAACATCGACCACTGCACTCCAGCCAGATCGGAAGAGCTCGTATGCCG

TCTTCTGCTTG

Clone 6

SEQ ID NO: 21

GATACGGCGACCACCGAGATCTACACTCTTTCCCTACACGACGCTCTTCC

GATCTCCACCCTGCCCTGCAAAACCACCAGCTCCGTGGTCTCTGGATGGG

ACTCCCAGGTGCCTGGGGAACCAAAACAAGAAAAAAATGGAGGAGAGTTT

TGAGCAAGAACTAAAGCCAAGGAAAGATGGGGAAGAGGCAAAGACTAGGA

ATAACAATAATCTTTAGAGCTGCTGGCATTCATTCATTCATCCAGATCGG

AAGAGCTCGTATGCCGTCTTCTGCTTG

Clone 7

SEQ ID NO: 22

AATGATACGGCGACCACCGAGATCTACACTCTTTCCCTACACGACGCTCT

TCCGATCTAGAAAATGAGATCGCTGATGGCTTGCAGTTGGCACGTGAAGG

AAAGTGAGGATAAAGAAGGACTTCCAGGTTTTTGTCTTGAGCAACTGGAA

ATACTGAGATGGGAAGACTGGGGGAGAAGCAGATTTGAAGGCTTTGGGGA

GGAGAGGGGAATCAGAAATGAAATTTCAGATTCTTTTTAAATATCCCTAG

TGGAGATGTTGAATAGGCAGTGGGTAAGTAGTCAGCAGCTTAGGGGAGAG

AAGAGGACGGAAATTTGAATTTGGGAAAGATTTAAATTTGGGGAACCATT

GATGGATATAAGTGGTATTTAAAGCCACAGGATTAGGCTGGGCACAGTGG

CTCATGCCTATAATCCCAGCCCTTTGGGAGGCTGAGGCAGGTGGATCACT

TGAGGCCAGGAGTTTGAGACCAGCCTGGCCAACATGGTGAAACCCTGTCT

CTACCAAAAAATACAGAAAATTAGCCGTGTGTGGTGGTGCGTGCCTGTAG

TCCCAGATACTCAGGAGGGTGAGGCAGGAGAATTGCTTGAATCCTGGAGG

CGGAGGTTACGGTGAGCCAAGATCATACCACTGCACTCAGATCGAAGAGC

TCGTATGCCGTCTTCTGCTTG

Clone 8

SEQ ID NO: 23

AATGATACGGCGACCACCGAGATCTACACTCTTTCCCTACACGACGCTCT

TCCGATCTGGTAAAAAAGTAGGTAAGTCTTTTAAGGAGTTTTCCTGCAAA

GCGGACAGAGAACTAGGTCTGGTGGTGGTCGTCAAAGGAGAACTTTTTTC

TCCCTCCTTCCCTCCCTTCCTCCTAGATACTTGCATGTGTTGTAAAGAGT

GAGCACAGTGGTACATCTTTTCTTAGCCACAGTCAGCTGCCCAGGAGCAG

TGCTGAATGGGCAGAGCTGGATTTTACAGGGTTGGGATTTTGCCAGGTGA

GTAAGATAGAGGGGAGAAGTGGGACCAGGGAGTTCCAGGTCTGTGAACGG

CCCTGGCTGAGGAGCTGGATCATGAAATCTGAGTCAAGTAAGAAGGAAAT

TGAGGACACGAGTTGGGTATTGCATAGTGTTACTGTGTTAAGGTCAGGGG

TCAAAGACTTACTGGCATGGAGTAACCAGAGTAAGTGAGCTGGAAAGATG

AGTTGTCAGATCGGAAGAGCTCGTATGCCGTCTTCTGCTTG

Clone 9

SEQ ID NO: 24

CAAGCAGAAGACGGCATACGAGCTCTTCCGATCTCAGGGAGGAGGTAGAG

AGGAGAAAGAGAGCAGCCCGGGAGCAAGTTCTACAGCCGGTCAGTGCTGA

GTTGTTGGAGCTGGACATCCGGGAGGTGTATCAGCCTGGCTCAGGTGAGT

GAGAGCAAGACAGGCATTGGGCTGGGGAAGGAGTTTGGAAAGGTAAAAGC

CGACTGTGAGGAAGGAGGGGTCTAGATCGGAAGAGCGTCGTGTAGGGAAA

GAGTGTAGATCTCGGTGGTCGCCGTATCATT

Clone 10

SEQ ID NO: 25

CAAGCAGAAGACGGCATACGAGCTCTTCCGATCTTGGAACAGCCGCTCTC

ACCTCAGTTCATCTGGGGAAGGGGCTACAAAGCAAACAATCTTTATTCAC

AATTGGGGTGGCAGAGGGGAGATACCCCCAGGTCAGTCCAAAAGCAAAGA

TACTGGGAGGGAAGATGGCGCTGGGCGAGGAACTCAGCACTCATCCTCAC

CCAGCAGGGCATAAGGGTTTCGGCCAGCCAGGCTGGACCCTGGAGCCGAG

GTTGGGGTCTCCTCATCCCCTTCTCCCTCCTCATCCGCATCCCGGTCCTC

CTCTCCCTCCTCCTCACAGGAGCTGCTCAGCTCTTCCTCTTCCTCCACCT

CCTCGTCACCTGCTGGCCCCACCCTGCCCTGCAAAACCACCAGCTCCGTG

GTCTCTGGATGGGACTCCCAGGTGCCTGGGGAACCAAAACAAGAAAAAAA

TGGAGGAGAGTTTTGAGCAAGAACTAAAGCCAAGGAAAGATGGGGAAGAG

GCAAAGACTAGGAATAACAATAATCTTTAGAGCTGCTGGCATTCATTCAT

TCATCCATTCATTCAACTTCCAGATCGGAAGAGCGTCGTGTAGGGAAAGA

GTGTAGATCTCGGTGGTCGCCGTATCATT

Clone 11

SEQ ID NO: 26

CAAGCAGAAGACGGCATACGAGCTCTTCCGATCTTGGAGTGCAGTGGCAC

AATCATAGCTCACTGCAGCCTTGAACTCTTGGGCTCAAGTGATCCTCCTG

CCTCAGCCTCTGAAGTAGCAGAGACTACAGGCACATACCACCACACTTGG

CTAGTTTTCTTTATCTTTTGTAAAGATGGGGTTTCACTATGTTGCCCACA

CTAGTCTTGAGCTCCTGGTCTCAAGCAATCCTCCCACCTCAGCCTCCCAA

AGCGCTGGGACTATATAGGCATGAGCCCTCACACATGGCCGTCATCCATT

CTTTTACTCAGGTATCAATGTCCTTATTTTTAAAATCAAAGTAACTAAGA

CTCAGAGTAGCAAATCACTTACTCAAGACCTCACAGCTGAGAAGAGGTGG

AATTTAACTCAGGCTGTCATGATCCTTCCACTGCAGCAGACGCCCTCTTC

TGCCTTGCCCACCGCCACTGGCAGAGATCACCCCTCAGACACCCTGGGGC

CTAATGAGACCTGATCGAGATCGGAAGAGCGTCGTGTAGGGAAAGAGTGT

AGACTCGGTGGTCGCCGTATCATT

Clone 12

SEQ ID NO: 27

CAAGCAGAAGACGGCATACGAGCTCTTCCGATCTCTCGCCTTTTACCCTT

CCCTGTCTCCTTTCCTCTCCTCAGAGATTCTGCCATTGATGAAGCTGCTG

TCCACTCACCCCTAGATTTTGTTGCATAGCCAGTAAGATCTCTGGCCTG

GAATGTTTTGGGGAAAACTGGAAGGACTGTGTTATGGGAGTGGGAGTATA

ACTGGTACCTGGTTAATGCTTTCCCTTTCCATTATTCTTTTCTTCCTCCA

GCCTGGGCAGAGAAACGTGGTTACAAGACAGCCAAGGCGGCTCGGAATGA

TGTGTACAGAGCAGCCAACAGTCTCTTGCGGCTGGCAGTGGACGGCCGCC

TCAGCCTGTGTTTTCATCCCCCAGGCTACAGTGAACAGAAAGGTCAGAGC

CCAGATATTCTTCCCCAGCCCCCTGCTATAGCGTAGGTAAAAGGGTGTGG

GCTTTGTGGCCACAGAGAGGGTCAGATCGGAAGAGCGTCGTGTAGGGAAA

GAGTGTAGATCTCGGTGGTCGCCGTATCATT

Clone 13

SEQ ID NO: 28

CAAGCAGAAGACGGCATACGAGCTCTTCCGATCTAGGAAAGTGAGGATAA

AGAAGGACTTCCAGGTTTTTGTCTTGAGCAACTGGAAATACTGAGATGGG

AAGACTGGGGAGAAGCAGATTTGAAGGCTTTGGGGAGGAGAGGGAATC

AGAAATGAAATTTCAGATTCTTTTTAAATATCCCTAGTGGAGATGTTGAA

TAGGCAGTGGGTAAGTAGTCAGCAGCTTAGGGAGAGAAGAGGACGGAAA

TTTGAATTTGGGAAAGATTTAAATTTGGGGAACCATTGATGGATCATAAG

TGGTATTTAAAGCCACAGGATTAGGCTGGGCACAGGGCTCATGCCTATAA

TCCCAGCCCTTTGGGAGGCTGAGGCAGGTGGATCACTTGAGGCCAGGAGT

TTGAGACCAGCCTGGCCAACATGGTGAAACCCTGTCTCTACCAAAAAATA

CAGAAAATTAGCCGTGTGTGGTGATGCGTGCCTGTAGTCCCAGATACTCA

GGAGGGTGAGGCAGGAGATCGGAAGAGCGTCGTGTAGGGAAAGAGTGTAG

ATCTCGGTGGTCGCCGTATCATT

Clone 14

SEQ ID NO: 29

CAAGCAGAAGACGGCATACGAGCTCTTCCGATCTGGGCTGGTGGGGCGGA

AAGTCGTGAGTGTCTCCAGAACCCCGGGCCATACCCGATACTTTCAGACC

TACTTTCTTACCCCCTCTGTGAAGCTCTGTGACTGCCCAGGCCTCATCTT

CCCATCTCTTCTGCCTAGGCAGTTGCAGGTATGACGGGGAGGGTGGGTAA

GGGAAAGAGAGAAGGTGGGACATTGAGGAAAGTACTGAGTGCTCATTTCC

CTCAGATCGGAAGAGCGTCGTGTAGGGAAAGAGTGTAGATCTCGGTGGTC

GCCGTATCATT

Clone 15

SEQ ID NO: 30

CAAGCAGAAGACGGCATACGAGCTCTTCCGATCTCACGCCTGTGGTCTCA

GCTACTCAGGAGGTTGAGGCACGAGAATCGCTTGAACCTGGGAGGATGAG

GTTGTAGTGAGCCAACATCGCACCACTGCACTCCAGCCCGGGTGAGGGAG

TGAGACTCTGTCTCAAAAACAAAAACAAAAAAAAACAAGGACAGATGGAA

CATGTTGTCACACATTGGGTGGTATGGGGTTCATCAGGCTGCACATGTAT

GTTCTGTGCATTTTTTTGTATGTTGTAGTTTACAGTTACAAAGAAGATAG

CAGGAAGAAATGGTGAAAAAGTAGGTAAGTCTTTTAAGGAGTTTTCCTG

CAAAGCGGAGATCGGAAGAGCGTCGTGTAGGGAAAGAGTGTAGATCTCGG

TGGTCGCCGTATCATT

Clone 16

SEQ ID NO: 31

GATACGGCGACCACCGAGATCTACACTCTTTCCCTACACGACGCTCTTCC

GATCTTGGAACAGCCGCTCTCACCTCAGTTCATCTGGGGAAGGGCTACA

AAGCAAACAATCTTTATTCACAATTGGGGTGGCAGAGGGGAGATACCCCC

AGGTCAGTCCAAAAGCAAAGATACTGGGAGGGAAGATGGCGCTGGGCGAG

GAACTCAGCACTCATCCTCACCCAGCAGGGCATAAGGGTTTCGGCCAGCC

AGGCTGGACCCTGGAGCCGAGGTTGGTCTCCTCATCCCCTTCTCCCTCCT

ATCCGCATCCCGGTCCTCCTCTCCCTCCTCCTCCTCACAGGAGCTGCTCA

GCTCTTCCTCTTCCTCCTCCTCCTCGTCACCTGCTGGCCCCACCCTGCCC

TGCAAAACCACCAGCTCCGTGGTCTCTGGATGGGACTCCCAGGTGCCTGG

GGAACCAAAACAAGAAAAAAATGGAGGAGAGTTTTGAGCAAGAACTAAAG

CCAAGGAAAGATGGAGATCGGAAGAGCTCGTATGCCGTCTTCTGCTTG

Clone 17

SEQ ID NO: 32

AATGATACGGCGACCACCGAGATCTACACTCTTTCCCTACACGACGCTCT

TCCGATCTAGAGAAAGGAAATAGTTGGAGAAGAGGAGGTCAAGGACTGAG

CCTTAGGACAAGCCAGCATTTAGTTGGGCAAAGGACAGTGAGAAGGAGGA

AAACCAAGGGAGCGTCCCAGAAGTCAAATGAAGAAGGTGTTTGAAGAGGA

AAGGAGGAATCAGCTGTGTCAACTGTTGCTGACAGGCCAAATGAGAGAAC

AGAGAGCTGCTCAGCAGGCTTGGCAATGTGAAGATCCGTGGTTTCAGTGG

GGTGGAGAAAGCCAAACTGGAGTAGGCCCATGAGAGAAGGTGCAACAACT

TCACATAACATTGTGTGAAAAGAGTCTGACCCAATAGCATCCATACTGCA

-continued

CAATTTCAGTTCTATCAAGTTTGAAAGCTGCAAAATTAAGCTGCATTGTT

GAGAGATACACAGGTCATAAACTAAAGAGAAATGTAAGGAGTTGATTTCC

TTAAAAGGATAAAGCTTGCATGTATAGAGGGAGAGGATTATGATCAAGAA

GGATGAGTGGCGGCCGGTATGGTGCCTCATCCCTGTAATCCTAGCACTTT

GGGAGGCTGAGGCAGGCGCAAGATCGGAAGAGCTCGTATGCCGTCTTCTG

CTTG

Clone 18

SEQ ID NO: 33

CAAGCAGAAGACGGCATACGAGCTCTTCCGATCTGGGATGAGGTCAGCAA

GATCACCAGGGCCCACATCATGTAGAGCCCTGAGGCTGTGACAGCCATTT

TGGATTTTATTCCAAGTCTCATGAGAAGCCAAGGGTAGGTTTTGAACAGG

GGAATGATAGGATCTGATTTTGTTTCTTATAAGTTTACCTCCTGAGTAGA

GAATAAATGATGGGGGGTGGGCAAGAAAGGGAGCAGAGAGAGCAGTTGAG

GCTATTTCAGTAATCTAGGAGAGAAATAAGAGTTGCTTAGAGTAGGATGC

TGGAGCTGGAGGTGGTGAGACAGGGCCGGAAGCATGATATATTTTGAAGG

TAGAGAAAATGAGATCGCTGATGGCTTGAGATCGGAAGAGCGTCGTGTAG

GGAAAGAGTGTAGATCTCGGTGGTCGCCGTATCATT

Clone 19

SEQ ID NO: 34

AATGATACGGCGACCACCGAGATCTACACTCTTTCCCTACACGACGCTCT

TCCGATCTGGGAGGACTGAACATCGGAAGAAGTTGAGTGGGATGAAAGGG

AGTCAGGCCGATGGGGGAGAGGGTCTTATGGCCCCTGAGAGCTGGCCAGC

ACTGGCGTCACCGGCCCCTCCCCGCAGGGCTTCAAGATGGGCTGCGCTCC

AGTTCCAACAGCCGCAGCGGGAGCCGGGAGCGGCGAGAGGAACAGACCGA

CACCTCGGACGGGGAGTCTGTGACCCATCATATCCGCAGGCTTAACCAGC

AGCCTTCTCAGGGGCTGGGTCCACGAGGCTACGACCCAAATCGGTGAGGG

TGGGAGGGGGCGCTGGTCCCGGCTTTCCCGCCTACCCGGAAGTCAGAGCT

TTGGGGAGATCGGAAGAGCTCGTATGCCGTCTTCTGCTTG

Clone 20

SEQ ID NO: 35

AATGATACGGCGACCACCGAGATCTACACTCTTTCCCTACACGACGCTCT

TCCGATCTGACCCAAATCGGTGAGGGTGGGAGGGGGCGCTGGTCCCGGC

TTTCCCGCCTACCCGGAAGTCAGAGCTTTGGGGGAAAGCGGGCTGCTACT

GGTGAAGACGGTGGGCCTGGGATGCCACAGTTCTCCGCTAGCCACTCGGC

TCCCCACAGCGGGCCACAGTCTTCCTTTCCAGAGGGGCTGGAGAGAGTTG

GGCTTTTAGAAGGAAGGCTGAGTATTGCCTGAAAGAAGGACTTGGGGG

AAGTCTGACTTGAGAGAGGAGACTTGAACGACTCTGGAGAGAATGGTTTG

CGAAGTTGATTGTACAAGAGGGGAGAAAATAGGAGTTTGTGGCCACAGGA

TTGCTCTGGATGTCTCGGTCCCTGTTCCCTTAGATACCGACTGCATTTTG

AGAGAGACAGCAGGGAGGAGGTAGAGAGGAGAAAGAGAGCAGCCCGGGAG

CAAGTTCAGATCGGAAGAGCTCGTATGCCGTCTTCTGCTTG

EXAMPLE 2

The DNA source used was a purified 10 kb region of Human BAC. The DNA was first prepared for ligation to forked adaptors by: fragmentation of the DNA by nebulisation, end repair of the DNA ends to make them blunt-ended and phosphorylation, then the addition of a single 'A' nucleotide onto the 3' ends of the DNA fragments. The ligation reaction was performed with the prepared fragmented DNA and adaptors pre-formed by annealing 'Oligo A' and 'Oligo B' (sequences given below). The product of the reaction was isolated/purified from unligated adaptor by gel electrophoresis. Finally, the product of the ligation reaction was subjected to cycles of PCR to selectively amplify ligated product that contained genomic DNA with adaptor at both ends of the fragments.

Materials and Methods

DNA Sample Preparation

Amplified 10 kb region of human BAC DNA (140K human chromosome 6 insert in a pTARBAC vector) using two primers (LRPCR primer 3: CGAGGAACTCAGCACTCATC SEQ ID NO:12 and LRPCR primer 4: ATGCCGAGGAA-GAAGCCATT SEQ ID NO:13). Used 0.3 µM each primer, 500 µM each dNTP, 0.08 ng/µl BAC DNA, 0.1 U/µl pfu ultra hotstart polymerase (Stratagene #600384) diluted in 1×pfu ultra hotstart buffer (Stratagene #600380).

PCR Programme:

| | |
|---|---|
| 92° C. 2 mins | |
| 92° C. 10 secs | |
| 58° C. 30 secs | 10 cycles |
| 68° C. 22 mins | |
| 92° C. 10 secs | |
| 58° C. 30 secs | 25 cycles |
| 68° C. 24 mins | |
| Hold at 4° C. | |

Gel purified 10 kb product on 0.7% TAE agarose gel, using Qiagen gel extraction kit (Qiagen #28706), according to manufacturer's instructions.

The purified PCR product was 3' tailed with dCTP, using the following: 1.5 µg of purified 10 kb product, 800 µM dCTP, 250 µM $CoCl_2$, (NEB #B0252S), 0.2 U/µl of Tdt (NEB #MO252L), diluted in 1×NEB4 buffer (NEB # B7004S), in a total volume of 50 µl. After a 30 minute incubation at 37° C., the reaction was heat inactivated at 70° C. for 10 mins. The tailed PCR product was purified from enzymes, buffer, etc. by loading the reaction mix on a Qiagen column (Qiagen #28104), and eluting in 80 µl EB (Qiagen).

Nebulization

Materials:
 10 kb region of human BAC, dCTP tailed (from above)
 Buffer [glycerol 53.1 ml, water 42.1 ml, 1 M TrisHCl (pH7.5) 3.7 ml, 0.5 M EDTA 1.1 ml]
 Nebulizer Invitrogen (#K7025-05)
 Qiagen columns PCR purification kit #28104
Mix: 70 µl (1.1 micrograms) of DNA
 700 µl Buffer
Procedure:
 Chilled DNA solution was fragmented in the nebulizer on ice for 6 minutes under 32 psi of pressure. The recovered volume was purified with a Qiagen PCR purification kit column and eluted in 30 µl of EB (Qiagen).

End-Repair

Materials:

| | |
|---|---|
| T4 DNA Polymerase | NEB #M0203S |
| 10×NEB 2 buffer | NEB #B7002S |
| 100× BSA | NEB #B9001S |
| dNTPs mix (10 mM each) | NEB #N0447S |

-continued

| E. coli DNA Pol I large fragment (Klenow) | NEB #M0210S |
| T4 polynucleotide kinase | NEB #M0201L |
| T4 PNK buffer | NEB #B0201S |
| 100 mM ATP | Amersham #27-2056-01 |
| Qiagen columns | PCR purification kit #28104 |

End repair mix was assembled as follows:

| DNA | 30 µl |
| Water | 7.5 µl |
| 10xNEB2 | 5 µl |
| 100xBSA | 0.5 µl |
| 10 mM dNTPs | 2 µl |
| T4 DNA pol (3 U/µl) | 5 µl |
| | 50 µl total |

The reaction was incubated for 15 min at room temperature, then 1 µl of E. coli DNA Pol I large fragment (Klenow) was added and the reaction incubated for a further 15 min at room temperature. The DNA was purified from enzymes, buffer, etc. by loading the reaction mix on a Qiagen column, and eluting in 30 µl EB (Qiagen). The 5' ends of the DNA were then phosphorylated using polynucleotide kinase as follows:

| DNA | 30 µl |
| Water | 9.5 µl |
| 10xPNK buffer | 5 µl |
| 100 mM ATP | 0.5 µl |
| T4 PNK (10 U/µl) | 5 µl |
| | 50 µl total |

The reaction was incubated for 30 min at 37° C., then heat inactivated at 65° C. for 20 min. DNA was then purified from enzymes, buffer, etc. by loading the reaction mix on a Qiagen column, and eluting in 30 µl EB (Qiagen).

A—Tailing Reaction
Materials:

| Taq DNA polymerase | NEB #M0267S |
| 10x thermopol buffer | NEB #B9004S |
| 1 mM dATP | Amersham-Pharmacia #272050 |
| Qiagen MinElute column | PCR purification kit #28004 |

The following reaction mix was assembled:

| DNA | 30 µl |
| 10x thermopol buffer | 5 µl |
| 1 mM dATP | 10 µl |
| Taq pol (5 U/µl) | 3 µl |
| | ~50 µl total |

The reaction was incubated for 30 min at 70° C., then the DNA purified from enzymes, buffer, etc. by loading the reaction mix on a Qiagen MinElute column, and eluting in 10 µl EB (Qiagen).

Anneal Forked Adaptor
Materials:

```
Oligo A:
                                        SEQ ID NO: 3
5'ACACTCTTTCCCTACACGACGCTCTTCCGATCxT
(x = phosphorothioate bond)

Oligo B:
                                        SEQ ID NO: 4
5'Phosphate-GATCGGAAGAGCTCGTATGCCGTCTTCTGCTTG
```

50 mM Tris/50 mM NaCl pH7
PCR machine

| 100 µM Oligo A | 20 µl |
| 100 µm Oligo B | 20 µl |
| Tris/NaCl | 10 µl |
| | 50 µl at 40 µM duplex in 10 mM Tris/10 mM NaCl (pH 7.5) |

The adaptor strands were annealed in a PCR machine programmed as follows:
Ramp at 0.5° C./sec to 97.5° C.
Hold at 97.5° C. for 150 sec
Then a step of 97.5° C. for 2 sec with a temperature drop of 0.1° C./cycle for 775 cycles
Forked adaptor was diluted to 15 µM final concentration in 10 mM Tris/10 mM NaCl pH 7.5.

Ligation Reaction
Materials:

| 15 µM forked adaptor (from above) | |
| A-tailed genomic DNA (from above) | |
| Quick Ligase | NEB #M2200S |
| Quick Ligase 2x buffer | NEB #B2200S |
| PCR machine | |
| Qiagen columns | PCR purification kit #28104 |

Reaction mix was assembled as follows:

| DNA | 10 µl |
| 2x buffer | 25 µl |
| 15 µM adaptor | 2 µl |
| Water | 8 µl |
| Quick Ligase | 5 µl |
| | 50 µl total |

The reaction was incubated for 30 min at room temperature then the DNA purified from enzymes, buffer, etc. by loading the reaction mix on a Qiagen column, and eluting in 30 µl EB (Qiagen).

Gel Purification
Materials:

| Agarose | Promega #V3841 |
| 100 base pair ladder | NEB #N3231L |
| TAE | |
| Loading buffer (50 mM Tris (pH 8), 40 mM EDTA, 40% w/v sucrose) | |
| Ethidium bromide | |
| Gel trays and tank. Electrophoresis unit | |
| Qiagen gel extraction kit | Qiagen #28706 |

The entire sample from the purified ligation reaction was loaded into one lane of a 4% agarose gel containing ethidium bromide and run at 120V for 90 min. The gel was then viewed on a 'White-light' box and fragments from 120 bp to 170 bp excised and purified with a Qiagen column, eluting in 30 μl EB (Qiagen).

Exonuclease I Treatment of PCR Primers

Exonuclease I (*E. coli*) NEB MO293S 20,000 Units/ml

Exonuclease I storage conditions:

100 mM NaCl, 10 mM Tris-HCl (pH 7.5), 0.5 mM EDTA, 5 mM 2-mercaptoethanol, 100 μg/ml BSA and 50% glycerol 1× Exonculease Reaction Buffer 67 mM Glycine-KOH 6.7 mM $MgCl_2$ 10 mM 2-mercaptoethanol (pH 9.5 @ 25° C.)

Protocol:

DNA Primers with a phosphorothioate at the n−1 position (5×85 μl of each Primer (approx 25 μM) were aliquoted into eppendorf tubes. 10 μl of 10× Exonuclease I Reaction Buffer and 5 μl of Exonuclease I was added to each tube. Each Eppendorf tube was placed in a rack and stored in an oven set at 37° C. for 16 hours. After 16 hr, the tubes were placed on a hotblock set at 80° C. for 2 minutes. Then the solutions from the eppendorfs were passed through P6 Bio Rad columns and spun in a centrifuge at 2000 rpm for 2 minutes. An extra 20 μl of $H_2O$ was added and the columns respun. The filtered solutions were placed into a speedvac and evaporated until each was at 20 μl, and the fractions combined. The pooled fractions were injected into a reverse phase HPLC system, and the main peak was collected. The collected fractions were evaporated to dryness in a speedvac, 50 μl of water was added and the fraction was subjected again to evaporation to dryness. The resulting pellets were dissolved in 50 μl of water, pooled and the UV measurement taken to determine the concentration of the oligonucleotide.

PCR Amplification

Materials:

Gel purified ligated DNA (from above)

PCR PRIMER 3:
SEQ ID NO: 9
exonuclease I treated
5'AATGATACGGCGACCACCGAGATCTACACTCTTTCCCTACACGACGCT
CTTCCGATCxT,
where x = phosphorothioate bond PCR PRIMER 4:
SEQ ID NO: 10
exonuclease I treated
5'CAAGCAGAAGACGGCATACGAGCTCTTCCGATCxT,
where x = pohosohorothioate bond

| 2x Phusion ™ PCR mix | NEB/Finnzymes #F531 |
|---|---|
| PCR machine | |
| Qiagen MinElute column | PCR purification kit #28004 |

The PCR reaction was prepared as follows:

| DNA | 0.5 μl |
|---|---|
| 2x Phusion ™ PCR mix | 12.5 μl |
| 8 μM PCR primer 3 | 1.5 μl |
| 25 μM PCR primer 4 | 0.5 μl |
| Water | 10 μl |
| | 25 μl total |

Thermocycling was carried out in a PCR machine under the following conditions:

30 sec @ 98° C.

[10 sec@ 98° C., 30 sec @ 65° C., 30 sec @ 72° C.] 18 cycles 5 min @ 72° C.

Hold @ 4° C.

PCR products were purified from enzymes, buffer, etc. on a Qiagen minelute column, eluting in 10 μl EB (Qiagen). The resulting DNA library was then ready for amplification on a surface amplification platform.

Validation of Library by Gel Analysis

20% of total library was run on a 4-20% TBE PAGE gel (Invitrogen #EC62252) and stained in Vistra green stain according to manufacturer's instructions (Amersham, RPN5786). The stained DNA was visualised using a Typhoon scanner and shown below.

Figure 3:
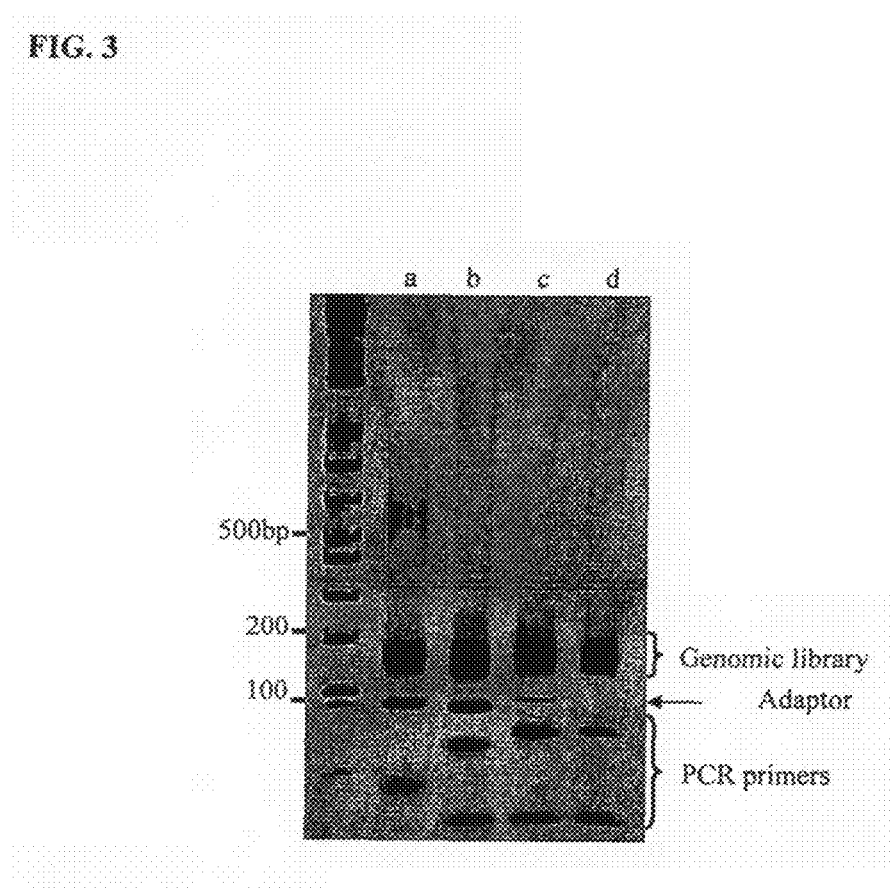
FIG. 3 shows a scan of a polyacrylamide gel stained to visualize DNA following electrophoresis. The lanes are as follows: M) marker lane; a) Amplification of library using unmodified PCR primers; b) Amplification of library using unmodified long PCR primers; c) Amplification of library using PCR primers having a phosphorothioate bond modification;
d) Amplification of library using exonuclease I treated PCR primers, which have a phosphorothioate modification.

The library was amplified (visualised as a smear from 150-200 bp) and no adaptor dimer (forked adaptor that has ligated to itself) was visible by eye using PCR primers 3 and 4 (from above), which have a phosphorothioate modification and were exonuclease I treated. Using the other 3 sets of primers (unmodified and modified with 3' phosphorothioate, but not exonuclease treated), the genomic library was amplified, but so was the adaptor dimer. The exonuclease I treated primer with 3' phosphorothioate modification prevents adaptor dimer amplification with Phusion™ polymerase FIG. 3 shows a 4-20% TBE PAGE gel (Invitrogen, EC62252) of 20% of a total library, stained in Vistra green stain according to manufacturer's instructions (Amersham, RPN5786).

M) Marker Lane a) Amplification of library using unmodified PCR primers (AATGATACGGCGACCACCGAGATCTA-CACTCTTTCCCTACACGA SEQ ID NO:14 and CAAGCAGAAGACGGCATACGA SEQ ID NO:15).

b) Amplification of library using unmodified PCR primers (AATGATACGGCGACCACCGA-CACTCTTTCCCTACACGACGCTCTTCCGATCT SEQ ID NO:7 and CAAGCAGAAGACGGCATAC-GAGCTCTTCCGATCT SEQ ID NO:8).

c) Amplification of library using PCR primers, which have a phosphorothioate bond modification (AATGATACG-GCGACCACCGAGATCTACACTCTTTC-CCTACACGACGCTCTTCCG ATCxT SEQ ID NO:9 and CAAGCAGAAGACGGCATACGAGCTCTTC-CGATCxT SEQ ID NO:10, where x is a phosphorothioate bond).

d) Amplification of library using exonuclease I treated PCR primers, which have a phosphorothioate modification (see PCR amplification method above).

Validation of Library by Conventional Sanger Sequencing

4 μl of the library was cloned into a plasmid vector (Zero Blunt TOPO PCR cloning kit, Invitrogen #K2800-20) and plated out on agar, according to the manufacturer's instructions. Colonies were picked, mini-prepped and the cloned inserts sequenced by conventional Sanger sequencing.

These results confirm that the library preparation method produces a library of 'sequenceable' DNA templates containing a mixture of genomic fragments of different sequence, flanked by the two adaptors (AATGATACGGCGACCAC-CGAGATCTACACTCTTTCCCTACAC-GACGCTCTTCCGATCT SEQ ID NO:7 and AGATCG-GAAGAGCTCGTATGCCGTCTTCTGCTTG SEQ ID NO:11), required for cluster formation and SBS sequencing. The insert DNA from each of the clones sequenced was found to align to the human BAC reference sequence. The genomic DNA is amplified with low error rates by using Phusion™, a high fidelity polymerase. The adaptor sequences have no mutations/deletions at adaptor-genomic DNA boundaries, which should allow the hybridisation of the SBS sequencing primer and successful SBS sequencing of inserts. None of the clones were adaptor dimers (lacked genomic insert).

Conventional Sanger Sequencing of 20 Clones from Library.

Clone 1
SEQ ID NO: 36
AATGATACGGCGACCACCGAGATCTACACTCTTTCCCTACACGACGCTCT
TCCGATCTGCCGTGTGTGGTGGTGCGTGCCTGTAGTCCCAGATACTCAGG
AGGGTGAGGCAGGAGAATTGCTTGAATCCTGGAGGCGGAGGTTACGGTGA
GCCAAGATCATACCACTGCACTCCAGCCTGGGTGACAGAGCAAGACTTCG
TCAAAAAAAAAAAAAAAAAAGCCATGGAATTGGATGAGATGTAGGAGAGA
AAGGAAATAGTTGGAGAAGAGGAGGTCAAGGACTGAGCCTTAGGACAAGC
CAGCATTTAGTTGGGCAAAGGACAGTGAGAAGGAGGAAAACCAAGGGAGC
GTCCCAGAAGTCAAATGAAGAAGGTGTTTGAAGAGGAAAGGAGGAATCAG
CTGTGTCAACTGTTGCTGACAGGCCAAATGAGAGAACAGAGAGCTGCTCA
GCAGGCTTGGCAATGTGAAGATCCGTGGTTTCAGTGGGGTGGAGAAAGCC
AAACTGGAGTAGGCCCATGAGAGAAGGTGCAACAACTTCACATAACATTG
TGTGAAAAGAGTCTGACCCAATAGCATCCATACTGCACAATTTCAGTTCT
ATCAAGTTTGAAAGCTGCAAAATTAAGCTGCATTGTTGAGAGATACACAG
GTCATAAACTAAAGAGAAATGTAAGGAGTTGATTTCCTTAAAAGGATAAA
GCTTGCATGTATAGAGGGAGAGGATTATGATCAAGAAGGATGAGTGGCGG
CCGGTATGGTGGCTCATCCCTGTAATCCTAGATCGGAAGAGCTCGTATGC
CGTCTTCTGCTTG Clone 2
SEQ ID NO: 37
CAAGCAGAAGACGGCATACGAGCTCTTCCGATCTGTGGTGAGTGAGCAGA
GTGGCAGTGAGCCCCAAGGCTTCCAGTTTTCTCCTTGGACAAGTCATCGT
AATTATTATTATTTTTTGAGATGGAGTTTAGATCGGAAGAGCGTCGT
GTAGGGAAAGAGTGTAGATCTCGGTGGTCGCCGTATCATT Clone 3
SEQ ID NO: 38
AATGATACGGCGACCACCGAGATCTACACTCTTTCCCTACACGACGCTCT
TCCGATCTAAAACCTACCCTTGGCTTCTCATGAGACTTGGAATAAAATCC
AAAATGGCTGTCACAGCCTCAGGGCTCTACATAGATCGGAAGAGCTCGTA
TGCCGTCTTCTGCTTG Clone 4
SEQ ID NO: 39
CAAGCAGAAGACGGCATACGAGCTCTTCCGATCTGATAGGATCTGATTTT
GTTTCTTATAAGTTTACCTCCTGAGTAGAGAATAAATGATGGGGGGTGGG
CAAGAAAGGGAGCAGAGAGAGCAGTTGAGGCTATTTCAGTAATCTAGGAG
ATCGGAAGAGCGTCGTGTAGGGAAAGAGTGTAGATCTCGGTGGTCGCCGT
ATCA Clone 5
SEQ ID NO: 40
CAAGCAGAAGACGGCATACGAGCTCTTCCGATCTCCAGCAGGTGACGAGG
AGGAGGAGGAAGAGGAAGAGCTGAGCAGCTCCAGATCGGAAGAGCGTCGT
GTAGGGAAAGAGTGTAGATCTCGGTGGTCCGCCGTATCA Clone 6
SEQ ID NO: 41
CAAGCAGAAGACGGCATACGAGCTCTTCCGATCTGAGAGCAGTTGAGGCT
ATTTCAGTAATCTAGGAGAGAAATAAGAGTTGCTTAGAGTAGGATGCTGG
AGCTAGATCGGAAGAGCGTCGTGTAGGGAAAGAGTGTAGATCTCGGTGGT
CGCCGTATCATT Clone 7
SEQ ID NO: 42
CAAGCAGAAGACGGCATACGAGCTCTTCCGATCTCTCCCACCCTCACCGA
TTTGGGTCGTAGCCTCGTGGACCCAGCCCCTGAGAAGGCTGCTGGTTAAG
CCTGCGGATATGAGATCGGAAGAGCGTCGTGTAGGGAAAGAGTGTAGATC
TCGGTGGTCGCCGTATCA Clone 8
SEQ ID NO: 43
CAAGCAGAAGACGGCATACGAGCTCTTCCGATCTAGGTGAGTGAGAGCAA
GACAGGCATTGGGCTGGGGAAGGAGTTTGGAAAGGTAAAAGCCGACTAGA
TCGGAAGAGCGTCGTGTAGGGAAAGAGTGTAGATCTCGGTGGTCGCCGTA
TCATT Clone 9
SEQ ID NO: 44
AATGATACGGCGACCACCGAGATCTACACTCTTTCCCTACACGACGCTCT
TCCGATCTTGCACTCCAGCCCGGGTGAGGGAGTGAGACTCTGTCTCAAAA
ACAAAAACAAAAAAAAACAAGGACAGATGGAACATGTTGTCACACATTGG
GTGGTATGGGGTTCATCAGGCTGCACATGTATGTTCTGTGCATTTTTTTG
TATGTTGTAGTTTACAGTTACAAAGAAGATAGCAGGAAGAAATGGTGAAA
AAAGTAGGTAAGTCTTTTAAGGAGTTTTCCTGCAAAGCGGACAGAGAACT
AGGTCTGGTGGTGGTCGTCAAAGGAGAACTTTTTTCTCCCTCCTTCCCTC
CCTTCCTCCTAGATACTTGCATGTGTTGTAAAGAGTGAGCACAGTGGTAC
ATCTTTTCTTAGCCACAGTCAGCTGCCCAGGAGCAGTGCTGAATGGGCAG
AGCTGGATTTTACAGGGTTGGGATTTTGCCAGGTGAGTAAGATAGAGGGG
AGAAGTGGGACCAGGGAGTTCCAGGTCTGTGAACGGCCCTGGCTGAGGAG
ATCGGAAGAGCTCGTATGCCGTCTTCTGCTTG Clone 10
SEQ ID NO: 45
CAAGCAGAAGACGGCATACGAGCTCTTCCGATCTGAAGCTCAGAGAAACG
TGCGTGATTCCAGGGAGGGTAGGGTCAAATGACTTTTGGGAGATTCTCTA
GATCGGAAGAGCGTCGTGTAGGGAAAGAGTGTAGATCTCGGTGGTCGCCG
TACATT Clone 11

SEQ ID NO: 46

CAAGCAGAAGACGGCATACGAGCTCTTCCGATCTGGAAATTCACAACCTA

GGACAGAGTTGATAAGAGGATGGAGCAGTGAAAGTCAACCCAGAGTTCTC

TAGATCGGAAGAGCGTCGTGTAGGGAAAGAGTGTAGATCTCGGTGGTCGC

CGTATCATT

Clone 12

SEQ ID NO: 47

CAAGCAGAAGACGGCATACGAGCTCTTCCGATCTAATAAGAGTTGCTTAG

AGTAGGATGCTGGAGCTGGAGGTGGTGAGACAGGGCCGGAAGCATGATAT

ATTAGATCGGAAGAGCGTCGTGTAGGGAAAGAGTGTAGATCTCGGTGGTC

GCCGTATCATT

Clone 13

SEQ ID NO: 48

AATGATACGGCGACCACCGAGATCTACACTCTTTCCCTACACGACGCTCT

TCCGATCTCGTGTGTGGTGGTGCGTGCCTGTAGTCCCAGATACTCAGGAG

GGTGAGGCAGGAGAATTGCTTGAATCCTAGATCGGAAGAGCTCGTATGCC

GTCTTCTGCTTG

Clone 14

SEQ ID NO: 49

CAAGCAGAAGACGGCATACGAGCTCTTCCGATCTAAAGCAATGAAAGGGG

ATAGAGAGTGACTGAGAGGAGAGGTGCTCAGGGAAAACCTCCCTGAGGAG

AGAACTGGATGATGAGATGAAGTGAGCCATTCAGAACTGTGGGGAGATCG

GAAGAGCGTGTGTAGGGAAAGAGTGTAGATCTCGGTCGTCGCCGTATCAT

T

Clone 15

SEQ ID NO: 50

CAAGCAGAAGACGGCATACGAGCTCTTCCGATCTTAAAAGGATAAAGCTT

GCATGTATAGAGGGAGAGGATTATGATCAAGAAGGATGAGTGGCGGCCGG

TATGGTGGCAGATCGGAAGAGCGTCGTGTAGGGAAAGAGTGTAGATCTCG

GTGGTCGCCGTATCATT

Clone 16

SEQ ID NO: 51

CAAGCAGAAGACGGCATACGAGCTCTTCCGATCTCTGAGATGGGAAGACT

GGGGGAGAAGCAGATTTGAAGGCTTTGGGGAGGAGAGGGGAATCAGAAAT

GAAATTTCAGATTCTAGATCGGAAGAGCGTCGTGTAGGGAAAGAGTGTAG

ATCTCGGTGGTCGCCGTATCATT

Clone 17

SEQ ID NO: 52

AATGATACGGCGACCACCGAGATCTACACTCTTTCCCTACACGACGCTCT

TCCGATCTGAGAGGTGAGTTGGCAGGGGACAAAGGGGAGAACAGAGAGGC

TTATTGACAAGGGGGCACCTGGTCTTGGGCCTAAGAGATCGGAAGAGCTC

GTATGCCGTCTTCGCTTG

Clone 18

SEQ ID NO: 53

CAAGCAGAAGACGGCATACGAGCTCTTCCGATCTCAAGAAAGGGAGCAGA

GAGAGCAGTTGAGGCTATTTCAGTAATCTAGGAGAGAAATAAGAGTTGCT

TAGAGTAGGATAGATCGGAAGAGCGTCGTGTAGGGAAAGAGTGTAGATCT

CGGTGGTCG

Clone 19

SEQ ID NO: 54

AATGATACGGCGACCACCGAGATCTACACTCTTTCCCTACACGACGCTCT

TCCGATCTAAAGCTTGCATGTATAGAGGGAGAGGATTATGATCAAGAAGG

ATGAGTGGCGGCCAGATCGGAAGAGCTGTATGCCGTCTTCTGCTTG

Clone 20

SEQ ID NO: 55

CAAGCAGAAGACGGCATACGAGCTCTTCCGATCTTCTACCAAAAAATACA

GAAAATTAGCCGTGTGTGGTGGTGCGTGCCTGTAGTCCAGATACTCAGGA

GGGTGAGGCAGGAGAGATCGGAAGAGCGTCGTGTAGGGAAAGAGTGTAGA

TCTCGGTGGTCGCCGTATCATT

Validation of Libraries by SBS Sequencing

Libraries were validated by SBS sequencing. Whole genomic BAC libraries were made using the method detailed in example 2 and sequenced by SBS sequencing. The protocols for preparing clusters on hydrogel surfaces and performing SBS sequencing are detailed in application WO06064199

The adaptor dimer contamination was reduced >300 fold by using PCR primers 3 and 4 (from above), which have a phosphorothioate modification and were exonuclease I treated, compared to using the shorter unmodified primers. The exonuclease I treated primer with 3' phosphorothioate modification prevents adaptor dimer amplification with Phusion™ polymerase.

SBS sequencing of genomic libraries amplified with a) unmodified shorter PCR primers (AATGATACGGC-GACCACCGAGATCTACACTCTTTCCCTACACGA SEQ ID NO:34 and CAAGCAGAAGACGGCAT-ACGA SEQ ID NO:35)

b) exonuclease I treated longer PCR primers, which have a phosphorothioate bond modification (AATGATACG-GCGACCACCGAGATCTACACTCTTTC-CCTACACGACGCTCTTCCG ATCxT SEQ ID NO:9 and CAAGCAGAAGACGGCATACGAGCTCTTC-CGATCxT SEQ ID NO:10, where x is a phosphorothioate bond).

Percentage of adaptor dimers in genomic libraries is reported.

| Library | Adaptor Dimer Contamination |
|---------|------------------------------|
| a)      | 9.95% +/− 1.45               |
| b)      | 0.03% +/− 0.02               |

While certain of the preferred embodiments of the present invention have been described and specifically exemplified above, it is not intended that the invention be limited to such embodiments. Various modifications may be made thereto without departing from the scope and spirit of the present invention, as set forth in the following claims.

The invention claimed is:

1. A method for generating a library of template polynucleotide molecules from one or more primary polynucleotide molecules, said method comprising:
   (a) providing blunt end target polynucleotide duplexes; and performing a tailing reaction to attach a single nucleotide overhang to the 3' ends of the blunt end target polynucleotide duplexes;
   (b) ligating an adaptor polynucleotide construct to both ends of the target polynucleotide duplexes to generate combined ligated adaptor-target-adaptor sequences;
   (c) preparing an amplification reaction comprising said combined ligated adaptor-target-adaptor sequences and at least two different primer oligonucleotides, wherein each of said at least two different primer oligonucleotides is complementary to at least a part of the adaptor polynucleotide construct sequence of the combined ligated adaptor-target-adaptor sequences, and complementary to the single nucleotide overhang attached to the target polynucleotide duplex, not extending beyond the single nucleotide overhang, and wherein a first primer of the two primer oligonucleotides is between 21-100 nucleotides in length and comprises a 5' sequence having the sequence of nucleotides 1-21 of SEQ ID NO: 6; and
   (d) performing an amplification reaction wherein said at least two different primer oligonucleotides anneal to complementary parts of the adaptor-target-adaptor sequences and are extended by sequential addition of nucleotides to generate a plurality of amplification products complementary to at least one strand of the combined ligated adaptor-target-adaptor sequences, wherein each of said plurality of amplification products has a first common sequence at its 5' end and a second common sequence at its 3' end, and wherein said plurality of amplification products comprises a library of template polynucleotide molecules.

2. The method of claim 1, wherein a second primer of the two primer oligonucleotides is between 20-100 nucleotides in length and comprises a 5' sequence having the sequence of nucleotides 1-20 SEQ ID NO: 5.

3. The method of claim 1, wherein the 5' sequence of the first primer comprises the sequence 5'-CAAGCAGAA-GACGGCATACGAGCTCTTCCGATCT-3' (SEQ ID NO:6).

4. The method of claim 2, wherein the 5' sequence of the second primer comprises the sequence 5'-AATGATACGGC-GACCACCGAGATCTACACTCTTTCC CTACAC-GACGCTCTTCCGATCT-3' (SEQ ID NO:5).

5. The method of claim 1, wherein the product of step (d) is subjected to solid phase amplification.

6. The method of claim 1, wherein providing blunt end target polynucleotide duplexes comprises fragmentation of the primary polynucleotide molecules by mechanical fragmentation.

7. The method of claim 1, wherein providing blunt end target polynucleotide duplexes comprises fragmentation of the primary polynucleotide molecules by chemical or enzymatic fragmentation.

8. The method of claim 1, wherein the one or more primary polynucleotide molecules are human genomic DNA molecules.

9. The method of claim 1, further comprising the steps of (e) preparing clusters from the library of template polynucleotide molecules; and (f) sequencing the clusters by sequencing by synthesis.

10. The method of claim 1, wherein the first primer of the two primer oligonucleotides is between 40-100 nucleotides in length.

11. The method of claim 1, wherein the first primer of the two primer oligonucleotides is between 21-40 nucleotides in length.

12. The method of claim 2, wherein the second primer of the two primer oligonucleotides is between 40-100 nucleotides in length.

13. The method of claim 2 wherein the second primer of the two primer oligonucleotides is between 20-40 nucleotides in length.

* * * * *